US010667930B2

(12) United States Patent
Folan et al.

(10) Patent No.: US 10,667,930 B2
(45) Date of Patent: *Jun. 2, 2020

(54) RETRIEVABLE STENT SYSTEM

(71) Applicant: BOSTON SCIENTIFIC SCIMED, INC., Maple Grove, MN (US)

(72) Inventors: Martyn G. Folan, Galway (IE); Thomas M. Keating, Galway (IE)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 92 days.

This patent is subject to a terminal disclaimer.

(21) Appl. No.: 15/936,651

(22) Filed: Mar. 27, 2018

(65) Prior Publication Data
US 2018/0280167 A1 Oct. 4, 2018

Related U.S. Application Data

(60) Provisional application No. 62/477,737, filed on Mar. 28, 2017.

(51) Int. Cl.
A61F 2/90 (2013.01)
A61F 2/958 (2013.01)
(Continued)

(52) U.S. Cl.
CPC ............... A61F 2/90 (2013.01); A61F 2/04 (2013.01); A61F 2/07 (2013.01); A61F 2/852 (2013.01); A61F 2/958 (2013.01); A61F 2002/0086 (2013.01); A61F 2002/044 (2013.01); A61F 2002/045 (2013.01); A61F 2002/075 (2013.01);
(Continued)

(58) Field of Classification Search
CPC .......... A61F 2002/075; A61F 2002/077; A61F 2/04; A61F 2002/044; A61F 2/07; A61F 2/852; A61F 2/82; A61F 2/90
See application file for complete search history.

(56) References Cited

U.S. PATENT DOCUMENTS 6,264,689 B1  7/2001  Colgan et al.
6,283,992 B1  9/2001  Hankh et al.
(Continued)

FOREIGN PATENT DOCUMENTS

WO   2004049982 A2   6/2004
WO   2015195893 A1   12/2015

OTHER PUBLICATIONS

International Search Report and Written Opinion dated Jun. 18, 2018 for International Application No. PCT/US2018/024456.
(Continued)

Primary Examiner — Jason-Dennis N Stewart
(74) Attorney, Agent, or Firm — Seager, Tufte & Wickhem, LLP

(57) ABSTRACT

A system for treating a body lumen including a first stent configured to be positioned in a body lumen and a second stent configured to be positioned in the lumen of the first stent prior to removing the first stent from the body lumen. The first stent includes a liner disposed radially inward of the tubular scaffold of the first stent to permit tissue ingrowth within a tissue ingrowth region defined between the liner and the tubular scaffold. The retrieval stent is configured to be expanded within the previously implanted first stent to cause tissue to recede from the tissue ingrowth region to facilitate removal of the first stent from the body lumen.

19 Claims, 21 Drawing Sheets

(51) Int. Cl.
- *A61F 2/07* (2013.01)
- *A61F 2/04* (2013.01)
- *A61F 2/852* (2013.01)
- A61F 2/95 (2013.01)
- A61F 2/82 (2013.01)
- A61F 2/00 (2006.01)

(52) U.S. Cl.
CPC . *A61F 2002/826* (2013.01); *A61F 2002/9528* (2013.01); *A61F 2210/0076* (2013.01); *A61F 2220/0025* (2013.01); *A61F 2230/001* (2013.01); *A61F 2250/0039* (2013.01); *A61F 2250/0051* (2013.01); *A61F 2250/0063* (2013.01); *A61F 2250/0098* (2013.01)

(56) References Cited

U.S. PATENT DOCUMENTS

| | | |
|---|---|---|
| 6,585,758 B1 | 7/2003 | Chouinard et al. |
| 7,311,031 B2 | 12/2007 | McCullagh et al. |
| 2003/0149472 A1 | 8/2003 | Pinchuk et al. |
| 2009/0210048 A1 | 8/2009 | Amplatz et al. |
| 2014/0121759 A1 | 5/2014 | Cully |
| 2014/0222039 A1 | 8/2014 | Khrosrovaninejad |
| 2014/0350694 A1 | 11/2014 | Behan |
| 2015/0045908 A1 | 2/2015 | McMahon |
| 2016/0095724 A1 | 4/2016 | Harris et al. |
| 2016/0296317 A1 | 10/2016 | Timmermans et al. |
| 2018/0250118 A1 | 9/2018 | Folan et al. |

OTHER PUBLICATIONS

Davee et al., "Stent-in-stent Technique for Removal of Embedded Partially Covered Self-Expanding Metal Stents", Surg Endosc, vol. 30, 2332-2341, 2016.

Deviere et al., "Anchoring System for Disease Treatment," Boston Scientific Corporation, 1-22, 2016.

Deviere et al., "Effectiveness of Endoscopic Management Using Self-Expandable Metal Stents in a Large Cohort of Patients with Post-bariatric Leaks," Obes Surg., vol. 25, 1569-1576, 2015.

Eisendrath et al., "Endotherapy Including Temporary Stenting of Fistulas of the Upper Gastrointestinal TractAfter Laparoscopic Bariatric Surgery," Endoscopy, vol. 39, 625-630, 2007.

International Search report and Written Opinion dated May 29, 2018 for International Application No. PCT/US2018/020474 (11 pgs).

U.S. Appl. No. 15/909,574, filed Mar. 1, 2018 (59 pgs).

Hirdes et al., "Stent-in-Stent Technique for Removal of Embedded Esophageal Self-Expanding Metal Stents," Am J Gastroenterol 2011; 106:286-293.

RETRIEVABLE STENT SYSTEM

CROSS-REFERENCE TO RELATED APPLICATIONS

This application claims priority to U.S. Provisional Application Ser. No. 62/477,737, filed Mar. 28, 2017, the entirety of which is incorporated herein by reference.

TECHNICAL FIELD

The present disclosure pertains to medical devices, methods for manufacturing medical devices, and the use thereof. More particularly, the present disclosure pertains to stents designed to be removed from the body and methods for manufacturing and using such stents.

BACKGROUND

Implantable medical devices (e.g., expandable stents) may be designed to provide a pathway for digested material, blood, or other fluid to flow therethrough following a medical procedure. Further, some implantable medical devices may incorporate features that aid in fistula treatment, bypass procedures and/or anastomosis treatment. These medical devices may include radially or self-expanding stents which may be implanted transluminally via an endoscope. Additionally, some stents may be implanted in a variety of body lumens such as the esophageal tract, the gastrointestinal tract (including the intestine, stomach and the colon), tracheobronchial tract, urinary tract, biliary tract, vascular system, etc.

In some instances it may be desirable to design a stent which includes sufficient radial strength to maintain its position within a body lumen while also having the ability to function as a passageway for food or other digested material to flow therethrough. However, in some stents, the compressible and flexible properties that assist in stent positioning may also result in a stent that has a tendency to migrate from its originally deployed position. For example, stents that are designed to be positioned in the esophageal or gastrointestinal tract may have a tendency to migrate due to peristalsis (i.e., the involuntary constriction and relaxation of the muscles of the esophagus, intestine, and colon which push the contents of the canal therethrough). Additionally, the generally moist and inherently lubricious environment of the esophagus, intestine, colon, etc. further contributes to a stent's tendency to migrate when deployed therein. One method to reduce stent migration may include exposing bare metal portions of the stent to the tissue of the body lumen. The stent scaffold may provide a structure that promotes tissue ingrowth into the interstices or openings thereof (e.g., the stent structure may promote a hyperplastic response). The tissue ingrowth may anchor the stent in place and reduce the risk of stent migration.

Additionally, while it is important to design stents that reduce the degree to which a stent migrates within a body lumen, it also important to design stents that may be easily removed and/or re-positioned from the body lumen post-deployment. Stents including bare portions (i.e., uncovered portions) designed to promote tissue ingrowth (e.g., to reduce stent migration as described above) may also be more difficult to remove once the tissue has anchored the stent in the body lumen. One method to reduce the force necessary to remove a stent from a body lumen may include positioning a covered, expandable secondary stent within the lumen of the primary (e.g., anchoring) stent. The radial expansion of the secondary stent within the lumen of the primary stent may cause the tissue ingrowth to recede, thereby reducing the force necessary to remove both the primary and secondary stents from the wall of the body lumen. Examples of secondary medical devices which are capable of being utilized with other medical devices are disclosed herein.

BRIEF SUMMARY

This disclosure provides design, material, manufacturing method, and use alternatives for medical devices. An example system for treating a body lumen includes a first stent. The first stent includes a first tubular scaffold, the first tubular scaffold including an inner surface. The first stent also includes an outer surface and a lumen extending therethrough and a liner disposed within the lumen of the first tubular scaffold, wherein the liner is configured to be radially spaced from the inner surface of the first tubular scaffold to permit tissue ingrowth along a portion of first tubular scaffold. The system also includes a second stent. The second stent includes a second tubular scaffold and a covering disposed on the second tubular scaffold, wherein the second stent is configured to be positioned within the first stent such that expansion of the second stent causes the tissue ingrowth to recede.

Alternatively or additionally to any of the embodiments above, wherein the second tubular scaffold is configured to expand radially outward, and wherein the radially outward expansion of the second tubular scaffold causes the tissue ingrowth to recede.

Alternatively or additionally to any of the embodiments above, wherein the first stent includes an inner surface having a first profile, and wherein the second stent includes an outer surface having a second profile, and wherein the first profile matches the second profile.

Alternatively or additionally to any of the embodiments above, wherein the second stent includes a first end region and a second end region, and wherein the first end region, the second end region, or both the first and second end regions have a flared portion.

Alternatively or additionally to any of the embodiments above, wherein the liner is configured to be radially spaced from a medial region of the first tubular scaffold to permit a tissue ingrowth region along the medial region, and wherein the second stent is configured to exert a radially outward expansion force along the tissue ingrowth region, wherein the radially outward expansion force is sufficient to cause the tissue ingrowth to recede.

Alternatively or additionally to any of the embodiments above, wherein the radially outward expansion force is 0.15 N or more.

Alternatively or additionally to any of the embodiments above, wherein the liner is configured to limit the amount of tissue ingrowth into the medial region of the tubular scaffold due to a hyperplastic response.

Alternatively or additionally to any of the embodiments above, wherein the tissue ingrowth region is formed between the inner surface of the tubular scaffold and an outwardly-facing surface of the liner.

Alternatively or additionally to any of the embodiments above, wherein the portion of the liner extending along the tissue ingrowth region is configured to deflect radially inward from the inner surface of the tubular scaffold.

Alternatively or additionally to any of the embodiments above, wherein the medial portion of the tubular scaffold includes a first inner diameter, and wherein the diameter of the liner along the tissue ingrowth region includes a second inner diameter, and wherein the second inner diameter is greater than 25% of the diameter of the first inner diameter.

Alternatively or additionally to any of the embodiments above, wherein the tissue ingrowth region extends circumferentially around the inner surface of the tubular scaffold.

Alternatively or additionally to any of the embodiments above, wherein a medial region of the tubular scaffold of the second stent has an outer diameter in a radially expanded state of the second stent greater than an inner diameter along a medial region of the tubular scaffold of the first stent in a radially expanded state of the first stent.

Another system for treating the esophagus includes:
a first stent including:
a first expandable scaffold, the first expandable tubular scaffold including an inner surface, an outer surface and a lumen extending therein; and
a liner disposed within the lumen of the first expandable scaffold, wherein the liner is configured to be radially spaced from a medial region of the first expandable scaffold to define a tissue ingrowth region along a portion of first expandable scaffold; and
a second stent including:
a second expandable scaffold and a covering disposed on the second expandable scaffold;
wherein the second stent is configured to be positioned within the first stent such that expansion of the second stent causes the tissue ingrowth to recede along the tissue ingrowth region.

Alternatively or additionally to any of the embodiments above, wherein the second expandable scaffold is configured to expand radially outward, and wherein the radially outward expansion of the second expandable scaffold causes the tissue ingrowth to recede.

Alternatively or additionally to any of the embodiments above, wherein the second stent is configured to exert a radially outward expansion force along the tissue ingrowth region, wherein the radially outward expansion force is sufficient to cause the tissue ingrowth to recede.

Alternatively or additionally to any of the embodiments above, wherein the radially outward expansion force is 0.15 N or more.

Alternatively or additionally to any of the embodiments above, wherein the first stent includes an inner surface having a first profile, and wherein the second stent includes an outer surface having a second profile, and wherein the first profile matches the second profile.

Alternatively or additionally to any of the embodiments above, wherein the portion of the liner extending along the tissue ingrowth region is configured to deflect radially inward from the inner surface of the tubular scaffold.

Alternatively or additionally to any of the embodiments above, wherein the liner extends continuously within the lumen of the first expandable scaffold.

An example method of treating a body lumen includes:
advancing a retrieval stent into the lumen of an implanted stent disposed along an inner surface of the body lumen, wherein a portion of tissue defining the inner surface of the body lumen has grown into the implanted stent, and wherein the implanted stent includes:
a liner disposed within the lumen of the implanted stent, wherein the liner is configured to be radially spaced from a medial region of the implanted stent to define a tissue ingrowth region along a portion of the implanted stent;
deploying the retrieval stent within the lumen of the implanted stent, wherein an outer surface of the retrieval stent exerts an outward radial force along the ingrown tissue region of the implanted stent, and wherein the retrieval stent causes the ingrown tissue to recede.

The above summary of some embodiments is not intended to describe each disclosed embodiment or every implementation of the present disclosure. The Figures and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
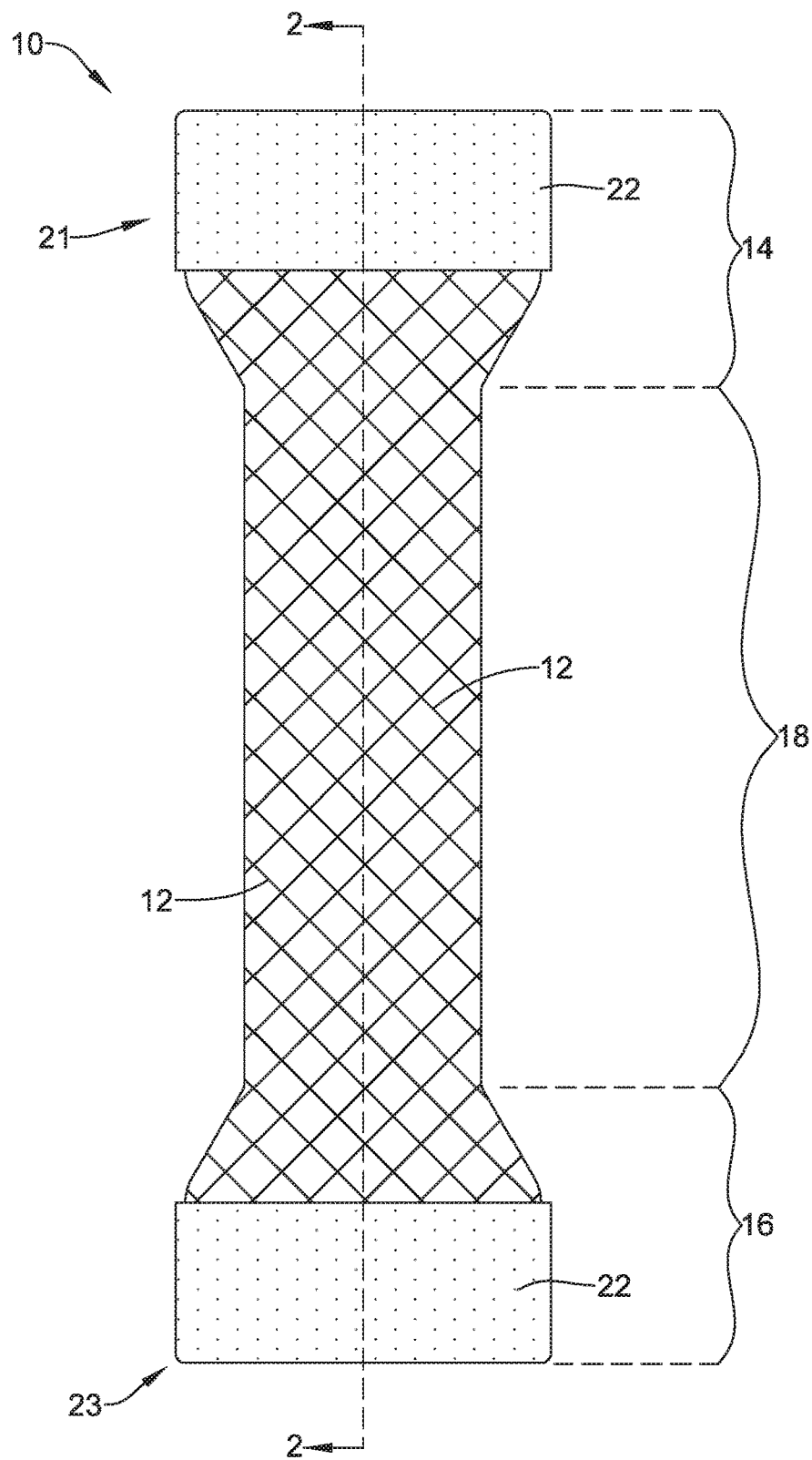
FIG. 1 is an example stent.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

As discussed above, in some instances it may be designed to provide a pathway for digested material, blood, or other fluid to flow therethrough following a medical procedure. Further, some implantable medical devices may incorporate features that aid in fistula treatment, bypass procedures and/or anastomosis treatment. These medical devices may include radially or self-expanding stents which may be implanted transluminally via an endoscope. Additionally, some stents may be implanted in a variety of body lumens such as the esophageal tract, the gastrointestinal tract (including the intestine, stomach and the colon), tracheobronchial tract, urinary tract, biliary tract, vascular system, etc.

In some instances it may be desirable to design a stent which includes sufficient radial strength to maintain its position within a body lumen while also having the ability to function as a passageway for food or other digested material to flow therethrough. However, in some stents, the compressible and flexible properties that assist in stent positioning may also result in a stent that has a tendency to migrate from its originally deployed position. For example, stents that are designed to be positioned in the esophageal or gastrointestinal tract may have a tendency to migrate due to peristalsis (i.e., the involuntary constriction and relaxation of the muscles of the esophagus, intestine, and colon which push the contents of the canal therethrough). Additionally, the generally moist and inherently lubricious environment of the esophagus, intestine, colon, etc. further contributes to a stent's tendency to migrate when deployed therein. One method to reduce stent migration may include exposing bare metal portions of the stent to the tissue of the body lumen. The stent scaffold may provide a structure that promotes tissue ingrowth (e.g., a hyperplastic response) into the interstices or openings thereof. The tissue ingrowth may anchor the stent in place and reduce the risk of stent migration.

Additionally, while it is important to design stents that reduce the degree to which a stent migrates within a body lumen, it also important to design stents that may be easily removed and/or re-positioned from the body lumen post-deployment. Stents including bare portions (i.e., uncovered portions) designed to promote tissue ingrowth (e.g., to reduce stent migration as described above) may also be more difficult to remove once the tissue has anchored the stent in the body lumen. One method to reduce the force necessary to remove a stent from a body lumen may include positioning a covered, expandable secondary stent within the lumen of the primary (e.g., anchoring) stent. The radial expansion of the secondary stent within the lumen of the primary stent may cause the tissue ingrowth to recede, thereby reducing the force necessary to remove both the primary and secondary stents from the wall of the body lumen. Examples of secondary medical devices which are capable of being utilized with other medical devices are disclosed herein.

FIG. 1 shows an example stent 10. Stent 10 may have a first end 21, a second end 23 and a lumen extending therein. When positioned in a body lumen (e.g., esophagus) first or proximal end 21 may be defined as the end of stent 10 closest to a patient's mouth and second or distal end 23 may be defined as the end of stent 10 closest to a patient's stomach.

Additionally, stent 10 may include one or more stent strut members 12 forming a tubular scaffold. Stent strut members 12 may extend helically, longitudinally, circumferentially, or otherwise along stent 10. While FIG. 1 shows stent strut members 12 extending along the entire length of stent 10, in other examples, the stent strut members 12 may extend only along a portion of stent 10.

Additionally, FIG. 1 shows example stent 10 including a first flared end region 14 proximate the first end 21 and/or a second flared region 16 proximate the second end 23 of stent 10. In some instances, first flared region 14 and second flared region 16 may be defined as an increase in the outer diameter, the inner diameter or both the inner and outer diameter along one or both of the first end 21 and/or second end 23 of stent 10. Further, FIG. 1 illustrates stent 10 including a medial region 18 positioned between first flared region 14 and second flared region 16.

However, it is contemplated that while FIG. 1 shows stent 10 including both a first flared region 14 and a second flared region 16, stent 10 may only include one flared region. For example, it is contemplated that stent 10 may include only flared region 14 or flared region 16. It is further contemplated that all or a portion of first flared region 14 and/or second flared region 16 may flare outwardly (e.g., away from the central, longitudinal axis of stent 10). Alternatively, it is further contemplated that all or a portion of first flared region 14 and/or second flared region 16 may flare inwardly (e.g., toward the central, longitudinal axis of stent 10).

In some instances, stent 10 may be a self-expanding stent or stent 10 may be a balloon expandable stent. Self-expanding stent examples may include stents having one or more struts 12 combined to form a rigid and/or semi-rigid stent structure. For example, stent struts 12 may be wires or filaments which are braided, wrapped, intertwined, interwoven, weaved, knitted, looped (e.g., bobbinet-style) or the like to form the stent structure. For example, while the example stents disclosed herein may resemble a braided stent, this is not intended to limit the possible stent configurations. Rather, the stents depicted in the Figures may be stents that are knitted, braided, wrapped, intertwined, interwoven, weaved, looped (e.g., bobbinet-style) or the like to form the stent structure. Alternatively, stent 10 may be a monolithic structure formed from a cylindrical tubular member, such as a single, cylindrical tubular laser-cut Nitinol tubular member, in which the remaining portions of the tubular member form the stent struts 12. Openings or interstices through the wall of the stent 10 may be defined between adjacent stent struts 12.

Stent 10 in examples disclosed herein may be constructed from a variety of materials. For example, stent 10 (e.g., self-expanding or balloon expandable) may be constructed from a metal (e.g., Nitinol, Elgiloy, etc.). In other instances, stent 10 may be constructed from a polymeric material (e.g., PET). In yet other instances, stent 10 may be constructed from a combination of metallic and polymeric materials. Additionally, stent 10 may include a bioabsorbable and/or biodegradable material.

In some instances, example stent 10 may include one or more layers positioned on and/or adjacent to the inner and/or outer surface of the tubular scaffold of stent 10. For example, FIG. 1 shows example stent 10 including an outer layer 22 (depicted as a dotted pattern in FIG. 1) disposed along a portion of the outer surface of stent 10 (e.g., along the first flared portion 14 and/or the second flared portion 16 of stent 10). In some instances, outer layer 22 may be an elastomeric or non-elastomeric material. For example, outer layer 22 may be a polymeric material, such as silicone, polyurethane, or the like.

Additionally, example stent 10 may include one or more layers positioned on and/or adjacent to the inner surface of stent 10. While not shown in FIG. 1 (but shown in FIG. 2), stent 10 may include an inner layer 20 disposed within the lumen of stent 10. In some instances, inner layer 20 may be an elastomeric or non-elastomeric material. For example, inner layer 20 may be a polymeric material, such as silicone, polyurethane, UE, PVDF, Chronoflex® or similar biocompatible polymeric formulations.

It can be appreciated that as inner layer 20 and outer layer 22 extend outwardly and inwardly, respectively, they may touch and/or form an interface region within the spaces (e.g., openings, cells, interstices) in the wall of tubular scaffolding of stent 10. Further, the inner layer 20 and outer layer 22 may additionally extend between adjacent struts 12, thereby filling any space between adjacent strut members 12 of the tubular scaffold. Stent 10 may include areas in which one or more filaments 12 are surrounded, encased and/or covered by the outer layer 22 and/or inner layer 20. For example, some portions of stent 10 may include filaments 12 which are sandwiched between outer layer 22 and inner layer 20.

Figure 2:
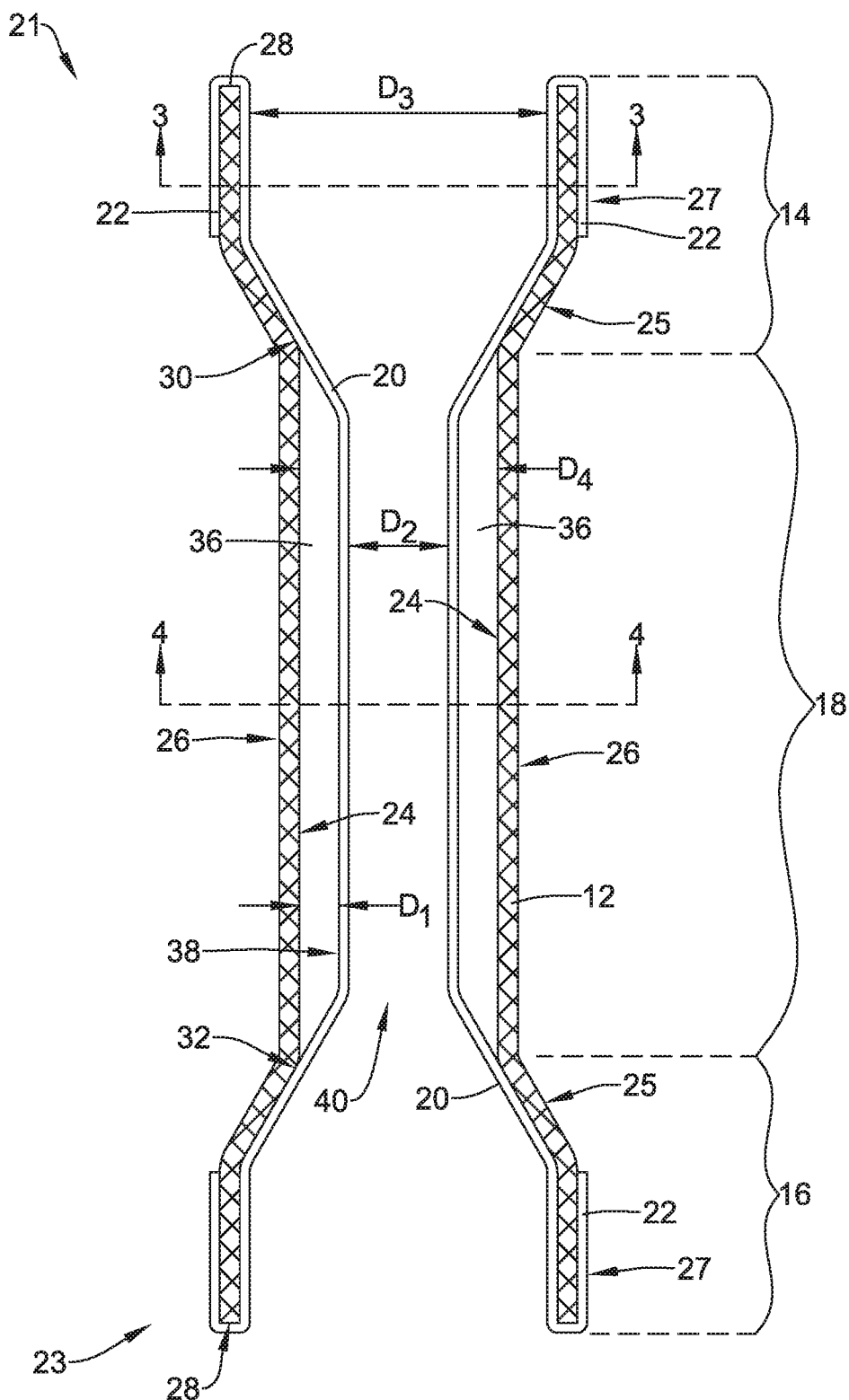
FIG. 2 is a cross-sectional view of the stent of FIG. 1 including a liner taken along line 2-2 of FIG. 1.

FIG. 2 shows a cross-section of example stent 10 along line 2-2 of FIG. 1. FIG. 2 illustrates that first flared region 14 and/or second flared region 16 may include tapered portion 25 and end portion 27. While FIG. 2 shows tapered portions tapering radially outward toward ends of stent 10, it is contemplated that one or more of tapered portions 25 may, alternatively, taper radially inward.

FIG. 2 further illustrates inner layer 20 extending along all or a portion of the inner surface 24 of stent 10. For example, FIG. 2 illustrates inner layer 20 extending along an inner surface of end portions 27, tapered portions 25 and medial portion 18. For purposes of the discussion herein, inner layer 20 may be interchangeably referred to as a liner, coating and/or covering. Liner 20 may extend circumferentially around the lumen of stent member 10. In other words, it can be appreciated that liner 20 may be defined as an annular layer that extends continuously around the lumen of stent member 10. Further, liner 20 may extend continuously (e.g., uninterrupted) around the lumen of stent 10, from the first end 21 to the second end 23.

As discussed above, FIG. 2 illustrates stent 10 may include an outer layer 22 disposed along an outer surface 26 of stent 10. For example, in some instances, stent 10 may include an outer layer 22 disposed along the outer surface of one or more of end portions 27.

In some instances (such as that illustrated in FIG. 2), outer layer 22 may be a continuous extension of inner layer 20. For example, FIG. 2 shows inner layer 20 extending along the inner surface 24 of end portions 27, whereby inner layer 20 "wraps" over the end 28 of the end portion 27 and continues to extend along the outer surface of end portion 27. It should be noted that, in this example, what has been described above as outer layer 22 may define the portion of the inner layer 20 which has "wrapped over" end 28 of tubular scaffold of stent 10 and further extends along the outer surface of end portion 27. Further, both the inner layer 20, and the portion of the inner layer 20 that wraps over end 28 of stent 10 to form outer layer 22 may, together, sandwich filaments 12 therebetween. Further, while FIG. 2 illustrates inner layer 20 wrapping around (e.g., extending continuously around) both end portions 27 of stent 10 in FIG. 2, it is contemplated that inner layer 20 may wrap around only one end portion 27 of stent member 10.

FIG. 2 illustrates that inner layer 20 may be fixedly attached to the inner surface of end portions 27 and/or tapered regions 25. In other words, FIG. 2 shows that inner layer 20 may be adhered (e.g., affixed, secured, etc.) to the inner surface of strut members 12 which define end portions 27 and/or tapered regions 25 of stent 10.

Additionally, FIG. 2 illustrates that, in some examples, a portion of inner layer 20 may be spaced away from (i.e., spaced radially inward of) the inner surface 24 of stent 10, providing a gap or space therebetween. In particular, FIG. 2 illustrates that the portion of inner layer 20 extending along the medial portion 18 of stent member 10 may be unattached to medial portion 18 of the tubular scaffold of stent 10 and spaced radially inward from the inner surface 24 of the tubular scaffold of stent 10. For example, FIG. 2 shows that liner 20 may be attached (e.g., circumferentially) at a first attachment point 30 and a second attachment point 32, with the length of liner 20 between attachment points 30/32 remaining unattached (i.e., not directly attached) to the tubular scaffold of medial portion 18 of stent 10. FIG. 2 shows that inner layer 20 may be unattached to the inner surface 24 of the tubular scaffold (i.e., the struts 12) of stent 10 along a portion of stent 10 between first attachment point 30 and second attachment point 32. It should be noted that the portion of stent 10 shown in FIG. 2 in which inner layer 20 is unattached to the inner surface 24 of struts 12 of stent 10 may correspond to the medial portion 18 of stent 10 described above. In other words, in some examples, inner layer 20 may be unattached and thereby extend radially inward from the inner surface 24 of the tubular scaffold (i.e., struts 12) along the medial portion 18 of stent 10.

As discussed above, stents that are designed to be positioned in a body lumen (e.g., esophageal or gastrointestinal tract) may have a tendency to migrate (due to peristalsis and/or the generally moist and inherently lubricious environment of the body lumens). Therefore, one method to reduce stent migration may include exposing tissue ingrowth promoting regions, such as uncovered and/or bare metal portions of the stent to the tissue of the body lumen. The uncovered or bare stent scaffold may provide a structure that promotes tissue ingrowth into the interstices or openings thereof. The tissue ingrowth may anchor the stent in place and reduce the risk of stent migration.

Accordingly, it can be appreciated that the portions of stent 10 discussed above which include an inner and/or outer layer which is attached (e.g., covers) stent struts or filaments 12 may act to prevent tissue from growing into the interstices or openings thereof. For example, the struts or filaments 12 of tapered regions 25 and end portions 27 of stent 10 which include inner layer 20 and/or outer layer 22 attached thereto to thereby span across interstices of the tubular scaffold may prevent tissue ingrowth along their respective surfaces and interstices therebetween.

However, it can be appreciated that tissue may be permitted to grow around, between, through, within, etc. those filaments 12 of stent 10 in which inner layer 20 is not attached (e.g., the portion of inner layer 20 extending along medial portion 18 of stent 10). In other words, FIG. 2 illustrates a "tissue ingrowth region" 36 defined along medial region 18 of stent 10. The detailed view of FIG. 2 illustrates that tissue ingrowth region 36 may be extend radially inward from the inner surface 24 of stent member 10 to the outer surface 38 of inner liner 20. The distance between the inner surface 24 of stent member 10 to the outer surface 38 of inner liner 20 may be depicted as "$D_1$" in FIG. 2. Distance "$D_1$" may be about 0.5 mm-10 mm, or about 1 mm-6 mm, or about 1.5 mm-4 mm, or about 2 mm.

FIG. 2 further illustrates that tissue ingrowth region 36 may be defined as the space between the inner surface 24 of the tubular scaffold of stent 10 and the outer surface 38 of liner 20 extending between attachment points 30/32. Tissue ingrowth region 36 may be positioned between attachment points 30/32. Thus, tissue ingrowth region 36 may be defined as a space between the inner surface 24 of the tubular wall defined by struts or filaments 12 of the stent 10 and the outer surface 38 of the wall of the inner layer 20 between the circumferential attachment points 30/32. Further, tissue ingrowth region 36 may be defined as extending circumferentially within the lumen of the tubular scaffold of stent 10. In other words, it can be appreciated that tissue ingrowth region 36 may be defined as an annular space that extends continuously around the lumen of the tubular scaffold formed by struts or filaments of stent 10 radially inward of the stent wall.

It can further be appreciated that liner 20 may be constructed from an elastic material in some instances. Accordingly, a liner 20 including an elastic material component may be able to stretch radially inward. For example, as tissue grows through the interstices of stent member 10, it may push radially inward against the outer surface 38 of inner layer 20. In response, inner layer 20 may deflect, stretch, etc. radially inward in response to inward forces (e.g., tissue ingrowth) acting thereupon. In particular, the space $D_1$ between the inner surface 24 of stent 10 and the outer surface 38 of liner 20 may increase as the liner 20 deflects radially inward. In other embodiments, the liner 20 may be inelastic and, therefore, may not deflect relative to stent 10.

While liner 20 may include an elastic element permitting it to deflect radially inward from the inner surface 24 of the tubular scaffold of stent 10, in some instances it may be desirable to limit the amount of deflection of inner layer 20. For example, FIG. 2 illustrates that inner layer 20 defines a lumen 40 extending therein. Lumen 40 may be designed to permit food and/or or other digestible material to flow therethrough. Therefore, in some instances it may be desirable to design inner layer 20 to preserve the passageway defined by lumen 40 to permit food and/or other digestible material to flow through stent 10 when implanted in a body lumen. In other words, it may be desirable in some instances to prevent lumen 40 from closing radially inward in on itself. In some instances the inner layer 20 may include reinforcing filaments (e.g., fibers) embedded in the material of the inner layer 20 that may be drawn taut after a threshold amount of stretching of the material of the inner layer 20 to prevent further stretching of the inner layer 20. In some instances, the reinforcement filaments may be arranged longitudinally, circumferentially, helically, randomly, or otherwise arranged in the inner layer 20.

FIG. 2 depicts an inner diameter of tubular scaffold of stent 10 along medial region 18 as "$D_4$." Further, FIG. 2 depicts an inner diameter of inner liner 20 along medial region 18 as "$D_2$." Diameter "$D_4$" may be about 10 mm-30 mm, or about 15 mm-25 mm, or about 20 mm, in some instances. Further, diameter "$D_2$" may be about 10 mm-30 mm, or about 15 mm-25 mm, or about 18 mm, in some instances. Additionally, in some instances, it may be desirable to design inner liner 20 such that the diameter "$D_2$" is greater than or equal to a given percentage of diameter "$D_4$." For example, in some instances diameter "$D_2$" may be greater than or equal to 10% of "$D_4$", or greater than or equal to 25% of "$D_4$", or greater than or equal to 50% of "$D_4$", or greater than or equal to 60% of "$D_4$", or greater than or equal to 75% of "$D_4$", or "$D_2$" may be between 10-20% of "$D_4$", or "$D_2$" may be between 20-30% of "$D_4$", or "$D_2$" may be between 30-40% of "$D_4$", or "$D_2$" may be between 40-50% of "$D_4$", or "$D_2$" may be between 50-75% of "$D_4$", or "$D_2$" may be between 75%-90% of "$D_4$", in some instances.

It can be appreciated that limiting the amount of deflection of inner liner 20 may not only assure that lumen 40 remains open, but it also limits that amount of tissue ingrowth occurring along stent 10. For example, by limiting the degree to which liner 20 may deflect radially inward along medial region 18, the amount of tissue ingrowth occurring along medial 18 may be controlled. As discussed above, controlling the amount of tissue ingrowth occurring along stent 10 may be desirable because the amount of tissue ingrowth may directly correspond to the force necessary to remove stent 10 from a body lumen. In other words, the stent 10 maybe customized to have a given removal force by limiting the amount of elasticity (e.g., and thereby limiting the amount of radially inward deflection) of liner 20.

As can be appreciated from FIG. 2, end portions 27 may include an inner diameter depicted as "$D_3$." Diameter "$D_3$" may be greater than or equal to diameter "$D_2$." Diameter "$D_3$" may be about 15 mm-35 mm, or about 20 mm-30 mm, or about 25 mm, in some instances. In other words, inner layer 20 may be generally shaped to taper longitudinally from the end portion 27 closest to first end 21 to the medial portion 18. For example, the tapered portion 25 may bear some resemblance to a cone-shaped funnel. Further, as illustrated in FIG. 2, stent 10 may taper inwardly toward central longitudinal axis of stent 10 along flared portion 14 and may taper outwardly away from the central longitudinal axis of stent 10 along flared portion 16.

Figure 3:
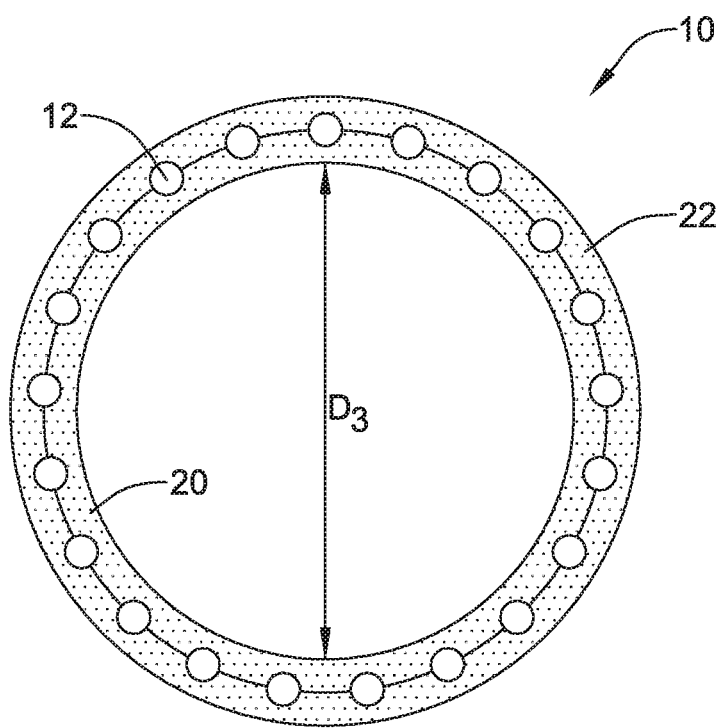
FIG. 3 is a cross-sectional view of the stent of FIG. 1 taken along line 3-3 of FIG. 2.

FIG. 3 illustrates a cross-section along line 3-3 of FIG. 2. As described above, this cross-section is taken through end portion 27 of flared region 14. As illustrated in FIG. 3, the filaments 12 of stent 10 defining end portion 27 may be sandwiched between inner layer 20 and outer layer 22. In other words, FIG. 3 illustrates that some portions of stent 10 (e.g., along flared region 14 and/or flared region 16), filaments 12 may have both inner layer 20 and outer layer 22 directly attached thereto. In other words, along some portions of stent 10 (e.g., along flared region 14 and/or flared region 16) no space may exist between filaments 12 and both inner layer 20 and outer layer 22.

Figure 4:
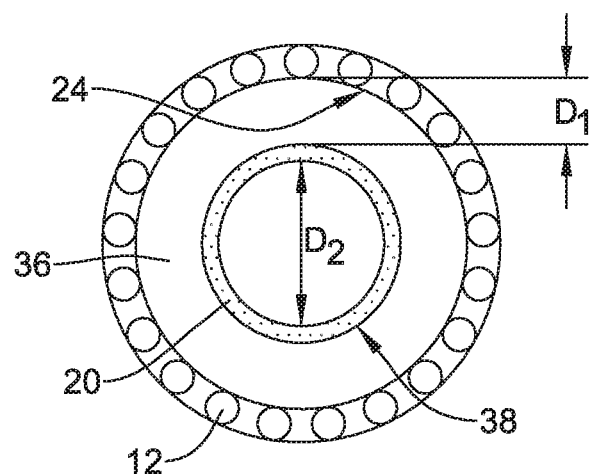
FIG. 4 is a cross-sectional view of the stent of FIG. 1 taken along line 4-4 of FIG. 2.

FIG. 4 illustrates a cross-section along line 4-4 of FIG. 2. As described above, this cross-section is taken through medial portion 18 of stent 10. As illustrated in FIG. 4, the inner layer 20 of stent 10 may be spaced away from (i.e., radially inward of) filaments 12 of stent 10 along medial portion 18. Further, FIG. 4 illustrates tissue ingrowth region 36 extending between the inner surface 24 of filaments 12 of stent 10 and the outwardly-facing surface 38 of inner member 20. Additionally, FIG. 4 illustrates tissue ingrowth region 36 extending circumferentially around the longitudinal axis of stent 10 radially outward of liner 20 and radially inward of filaments 12 of the tubular scaffold.

Figure 5:
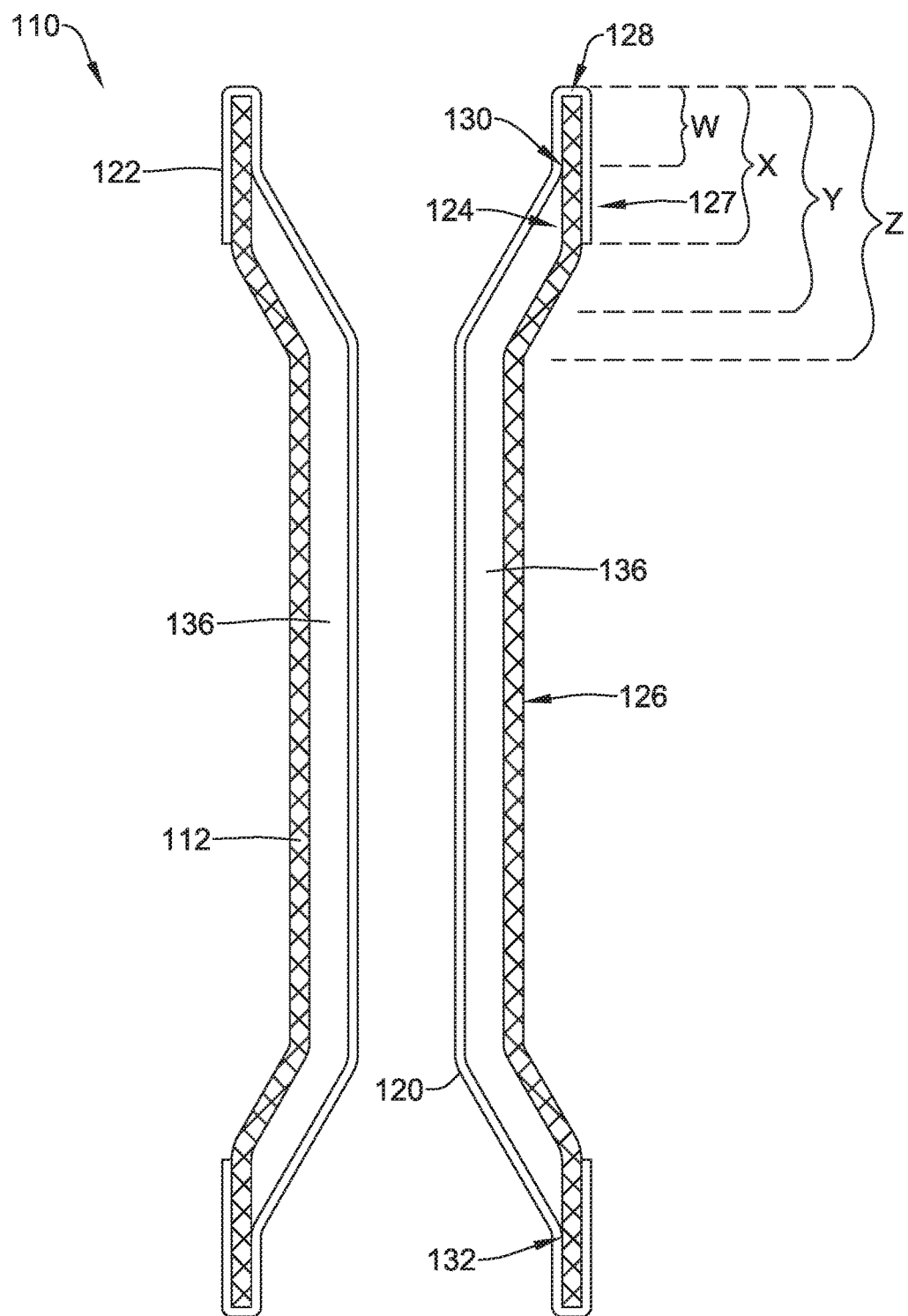
FIG. 5 is a cross-sectional view of the stent of FIG. 1 including a liner.

While the above discussion disclosed examples in which inner layer 20 and outer layer 22 are fixedly attached (e.g., directly secured) to the end portions 27 and/or tapered portions 25, other configurations are contemplated. For example, FIG. 5 illustrates an example stent member 110. Stent 110 may be similar in form and functionality to stent 10 described above. For example, stent 110 may include a liner 120 disposed within a lumen of the tubular scaffold of stent 110. Further, as illustrated in FIG. 5, liner 120 may be circumferentially attached along the inner surface 124 of stent 110 at attachment point 130 and/or attachment point 132. Attachment points 130/132 may be located at opposing end regions of stent 110, such as in opposing flared end regions of stent 110.

However, FIG. 5 illustrates that different attachment point locations 130/132 are contemplated along stent member 110. For simplicity purposes, example positions contemplated for attachment points 130/132 are depicted in terms of a distance from the end 128 of stent member 110. For example, the attachment points 130/132 are depicted as being a distance "W" (as measured along the outer surface 126 of stent 110) from end 128. In other examples, attachment points 130/132 may be positioned at distances depicted as "X," "Y" and "Z" (as measured longitudinally from end 128 of stent 110. Distance "Z" may be understood to be the equivalent attachment location of attachment points 30/32 along stent 110 described above. Additionally, in some examples distance "W" may be approximately 25% of distance "Z," distance "X" may be approximately 50% of distance "Z" and distance "Y" may be approximately 75% of distance "Z."

Additionally, it is contemplated that liner 120 may not be attached along the inner surface 124 of stent 110. For example, attachment points 130/132 may be located at the end point 128 of stent 110. Further, in instances where attachment points 130/132 are located at ends 128, liner 120 may cover and or encapsulate the ends 128 of stent 110.

It can be appreciated from FIG. 5 that the different attachment point 130/132 along stent 110 may correspond to different size tissue ingrowth regions 136 (described above as tissue ingrowth region 36 of stent 10). For example, the tissue ingrowth section 136 defined by attachment point 130/132 located a distance "W" from end 128 may be larger than a tissue ingrowth region 136 defined by attachment point 130/132 located a distance "Y" from end 128. For reasons discussed above, it can be appreciated that the larger tissue ingrowth regions may create a stent 110 which has increased removal forces.

Outer layer 122 may also extend any desired distance from end 128 of stent 110 along the outer surface of the tubular scaffold defined by filaments or struts 112. For example, outer layer 122 may extend a distance depicted as "W," "X," "Y" or "Z" from end 128. The distance outer layer 122 extends from end 128 of stent 110 may be the same or different than the distance for attachment points 130/132.

While the above discussion of stent 10 and stent 110 illustrates a variety of attachment locations along stent 10, it is contemplated that liner 20 may be attached at any location along the inner surface 24 and/or outer surface of stent member 10. The different attachment locations may result in stents having different performance characteristics (e.g., different removal forces, different anti-migration properties). It is noted that the attachment distances shown in FIG. 5 are equally applicable to the attachment point 132 at the opposite end of stent 110 and/or outer layer 122 at the opposite end of stent 110.

FIGS. 6A-8B illustrate example stents that may be similar in form and function to the stent designs disclosed above. For example, each of the stents shown in FIGS. 6A-8B may include an inner liner disposed within the lumen of the tubular scaffold of stent (e.g., as shown in FIG. 2). Further, each of the stents shown in FIGS. 6A-8B may also include an outer layer as described above (e.g., as shown in FIG. 1) extending along at least a portion of the flared end regions of the tubular scaffold. However, the stents illustrated in FIGS. 6A-8B may further include an additional outer layer (which could be formed separately or in conjunction with the outer layer disposed on the flared end regions and/or the inner layer) disposed along the outer surface of the medial portion of the stent, leaving a remainder of the tubular scaffold uncovered to promote tissue ingrowth therethrough.

Figure 6A:
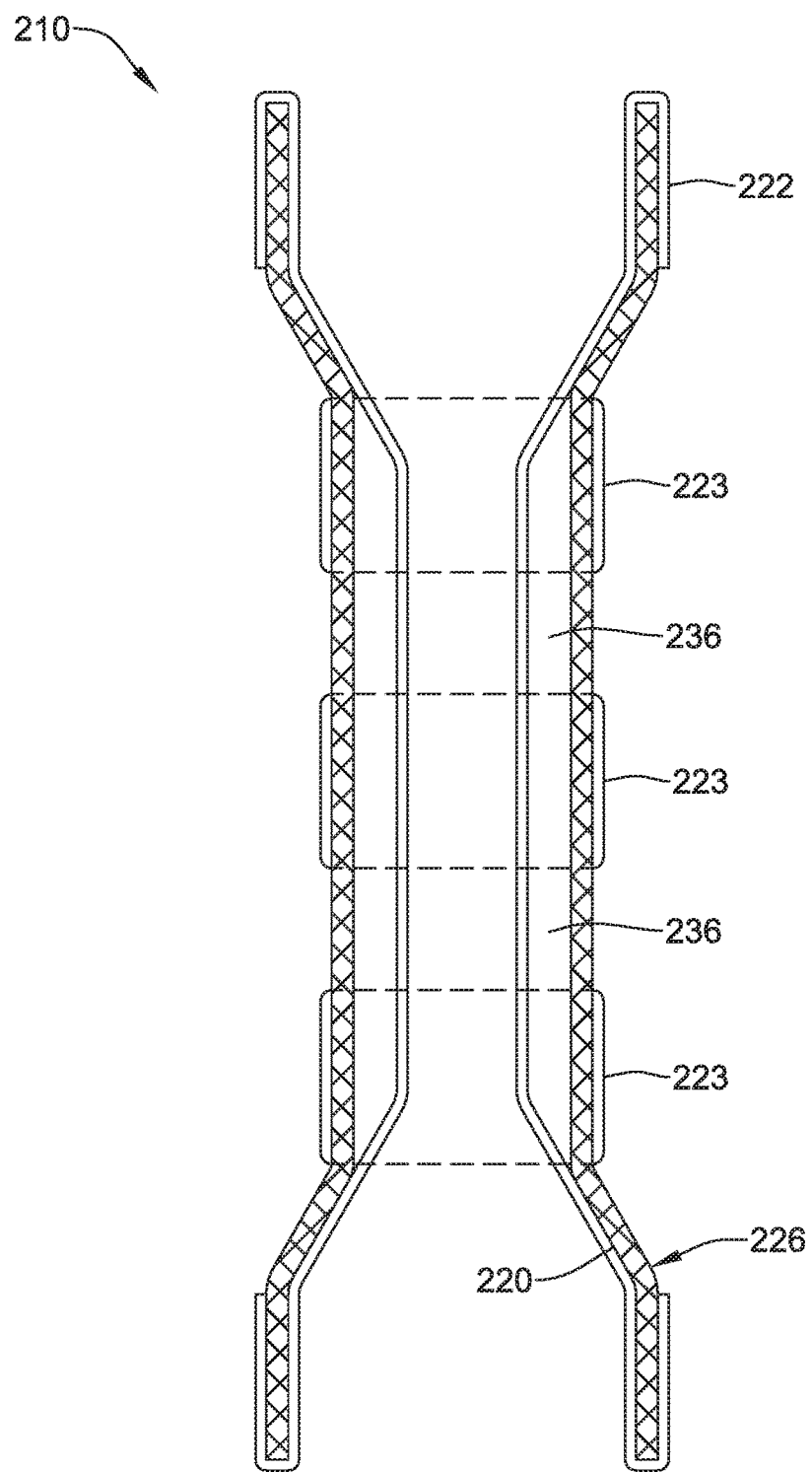
FIG. 6A is a cross-sectional view of another example stent including a liner and covered portions.
Figure 6B:
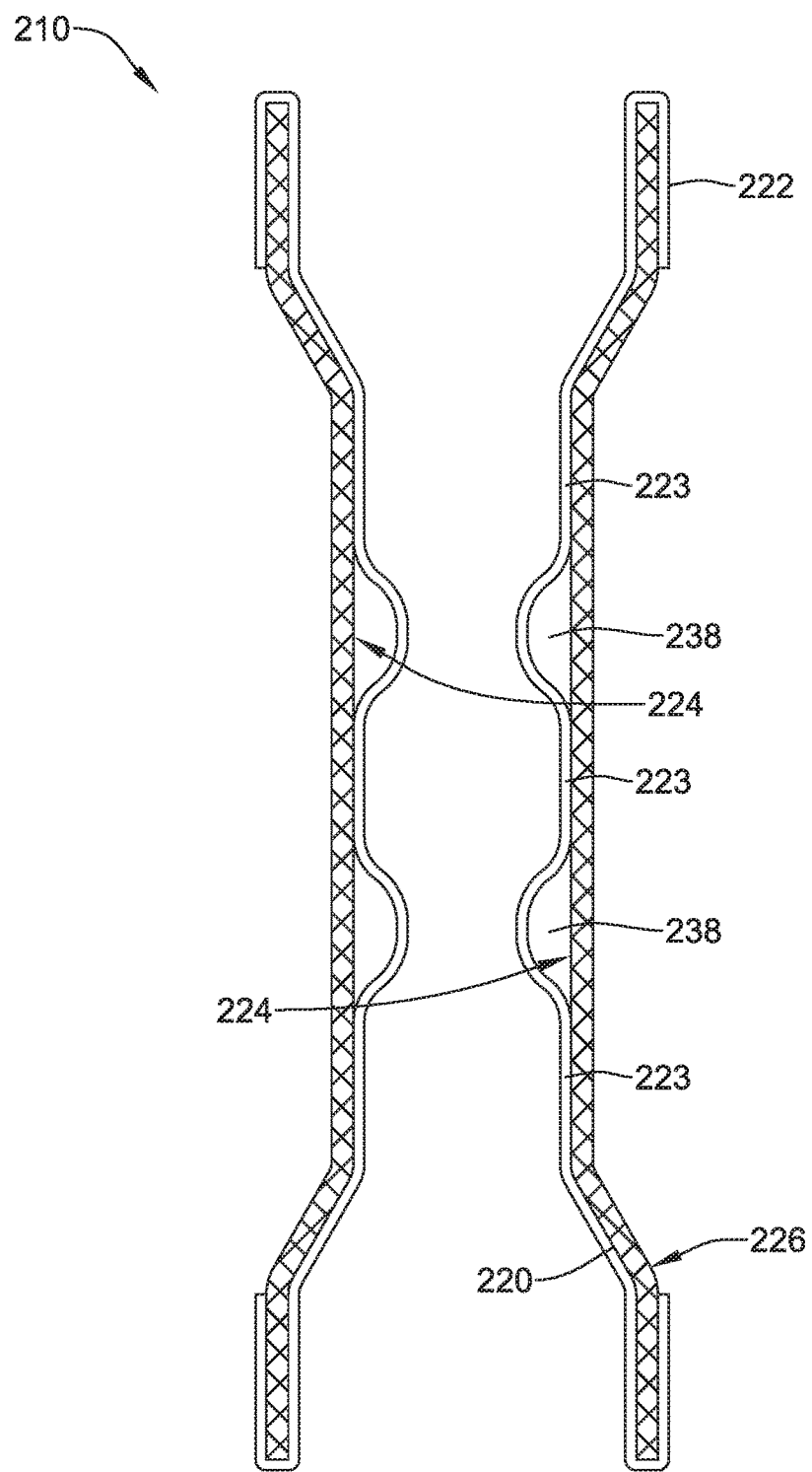
FIG. 6B is a cross-sectional view of another example stent including a liner and covered portions.
Figure 7A:
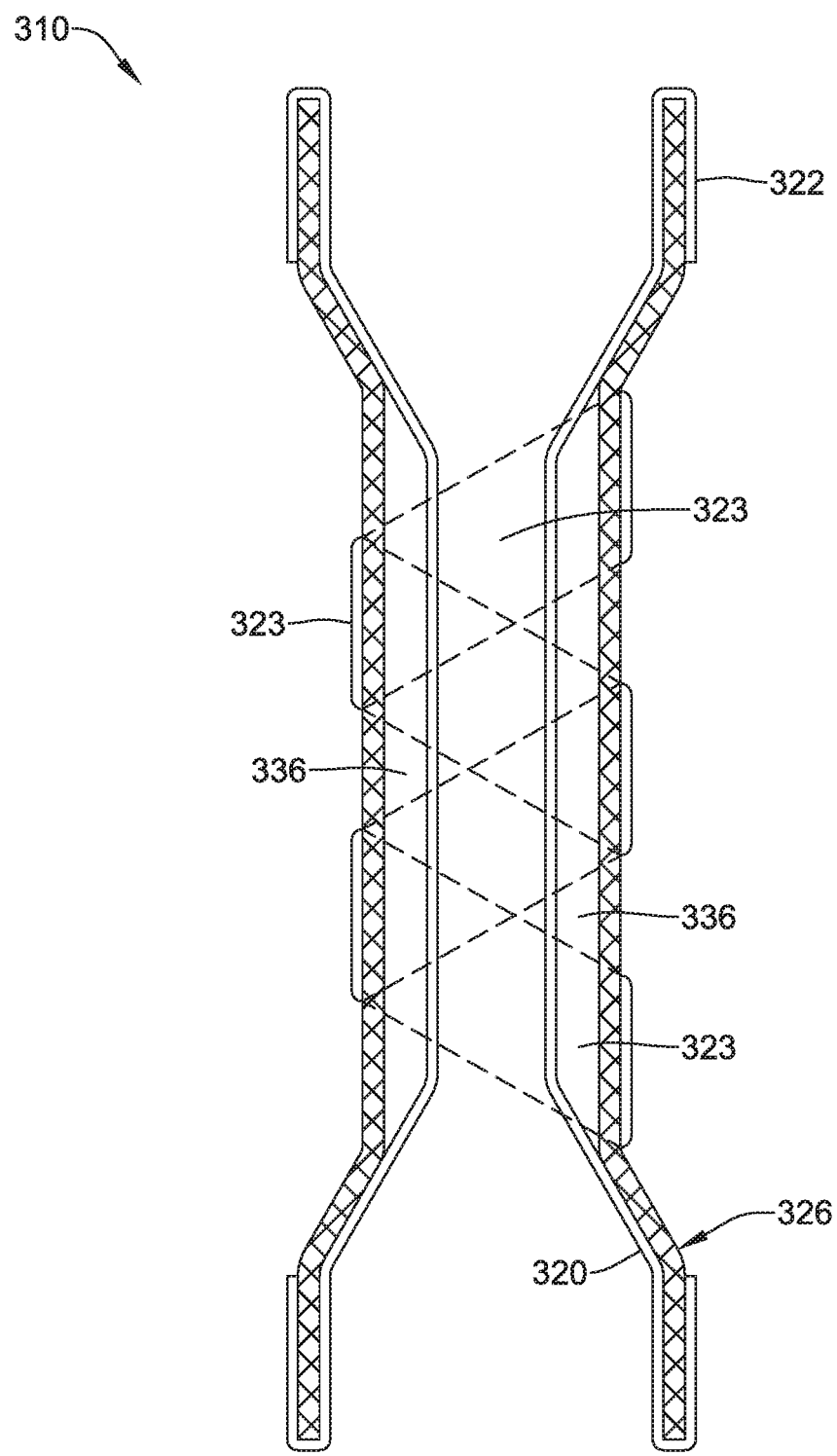
FIG. 7A is a cross-sectional view of another example stent including a liner and covered portions.
Figure 7B:
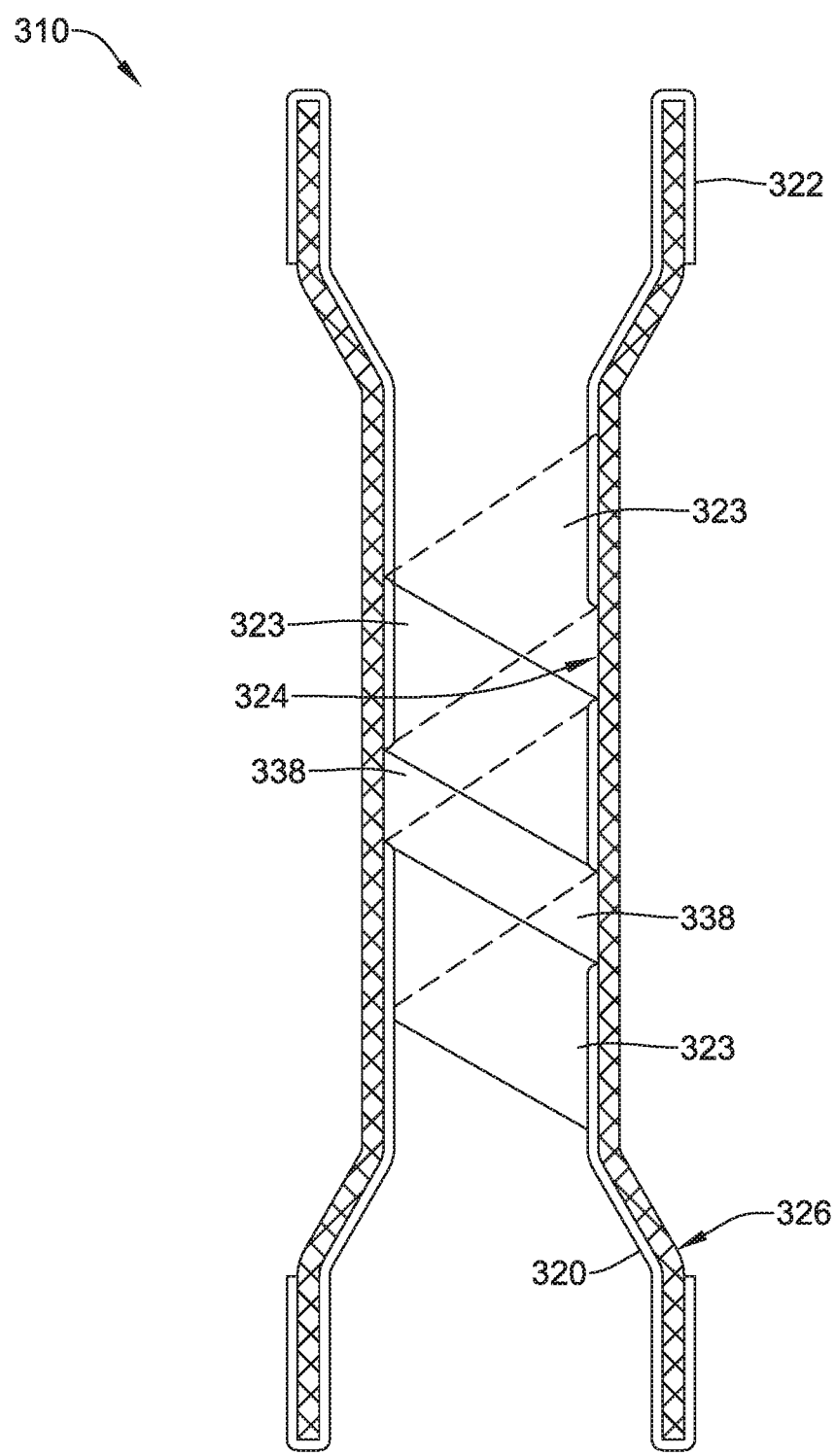
FIG. 7B is a cross-sectional view of another example stent including a liner and covered portions.

For example, FIG. 6A shows an example stent 210. Example stent 210 that may be similar in form and function to the stent designs disclosed above. However, as FIG. 6A illustrates, stent 210 includes additional outer layers 223 disposed along the outer surface 226 of the tubular scaffold of stent 210. FIG. 6A shows outer layers 223 as circumferential rings of material which may be positioned such that they extend circumferentially around the outer surface 226 of stent 210 (the dashed lines in FIG. 6A depict the outer layers 223 extending circumferentially around the outer surface 226 of stent 210) and spaced apart relative to one another. In some examples, outer layers 223 may be oriented such that they extend laterally across stent 210. As shown in FIG. 6A, individual outer layers 223 may be spaced longitudinally apart from one another. It can be appreciated that the configuration of outer layers 223 creates one or more tissue ingrowth regions 236 (similar to in function to those described above) along the medial region of stent 210. Tissue ingrowth regions 236 may be circumferentially uncovered portions of the tubular scaffold of stent 210. Inner layer 220 may be located radially inward of tissue ingrowth regions 236 to limit the amount a tissue ingrowth permitted.

Alternatively, some stent examples disclosed herein may be designed such that one or more portions of an inner layer extending along the inner surface of the stent may be spaced away from (i.e., spaced radially inward of) the inner surface of the stent, providing a gap or space therebetween. For example, FIG. 6B (which may be similar in form and function to the stent design disclosed above with respect to FIG. 6A) illustrates an alternative example stent having one or more portions of inner layer 220 extending along the inner surface 224 of stent 210 may be unattached to the inner surface of stent 210 and spaced radially inward from the inner surface 224 of the tubular stent 210 while other portions of the inner layer 220 are attached to the inner surface 224 of stent 210. The space created by the inner layer 220 extending radially inward of the inner surface 224 of the stent 210 may define one or more tissue ingrowth regions 238. Tissue ingrowth regions 238 may extend circumferentially around the inner surface 224 of stent 210.

FIG. 7 shows another example stent 310. Example stent 310 may be similar in form and function to the stent designs disclosed above. However, as FIG. 7 illustrates, stent 310 includes additional outer layer 323 disposed along the outer surface 326 of the tubular scaffold of stent 310. FIG. 7 shows outer layer 323 may be positioned such that it extends circumferentially around the outer surface 326 of stent 310

(the dashed lines in FIG. 7 depict outer layer 323 extending circumferentially around the outer surface 326 of stent 310). However, FIG. 7 shows that outer layer 323 may be oriented such that it extends in a helical configuration around the outer surface 326 of stent 310. It can be appreciated that the configuration of outer layer 323 creates one or more tissue ingrowth regions 336 (similar in form and function to those described above) along stent 310. Tissue ingrowth regions 336 may be circumferentially uncovered portions of the tubular scaffold of stent 310. Inner layer 320 may be located radially inward of tissue ingrowth regions 336 to limit the amount a tissue ingrowth permitted.

Alternatively, some stent examples disclosed herein may be designed such that one or more portions of an inner layer extending along the inner surface of the stent may be spaced away from (i.e., spaced radially inward of) the inner surface of the stent, providing a gap or space therebetween. For example, FIG. 7B (which may be similar in form and function to the stent design disclosed above with respect to FIG. 7A) illustrates an alternative stent example having one or more portions of inner layer 320 may extend in a helical orientation along and attached to the inner surface 324 of stent 310. It can be appreciated that the helical configuration of inner layer 320 creates one or more tissue ingrowth regions 338 (similar in form and function to those described above) along stent 310. Tissue ingrowth regions 338 may be helically oriented uncovered portions of the tubular scaffold of stent 310.

Figure 8A:
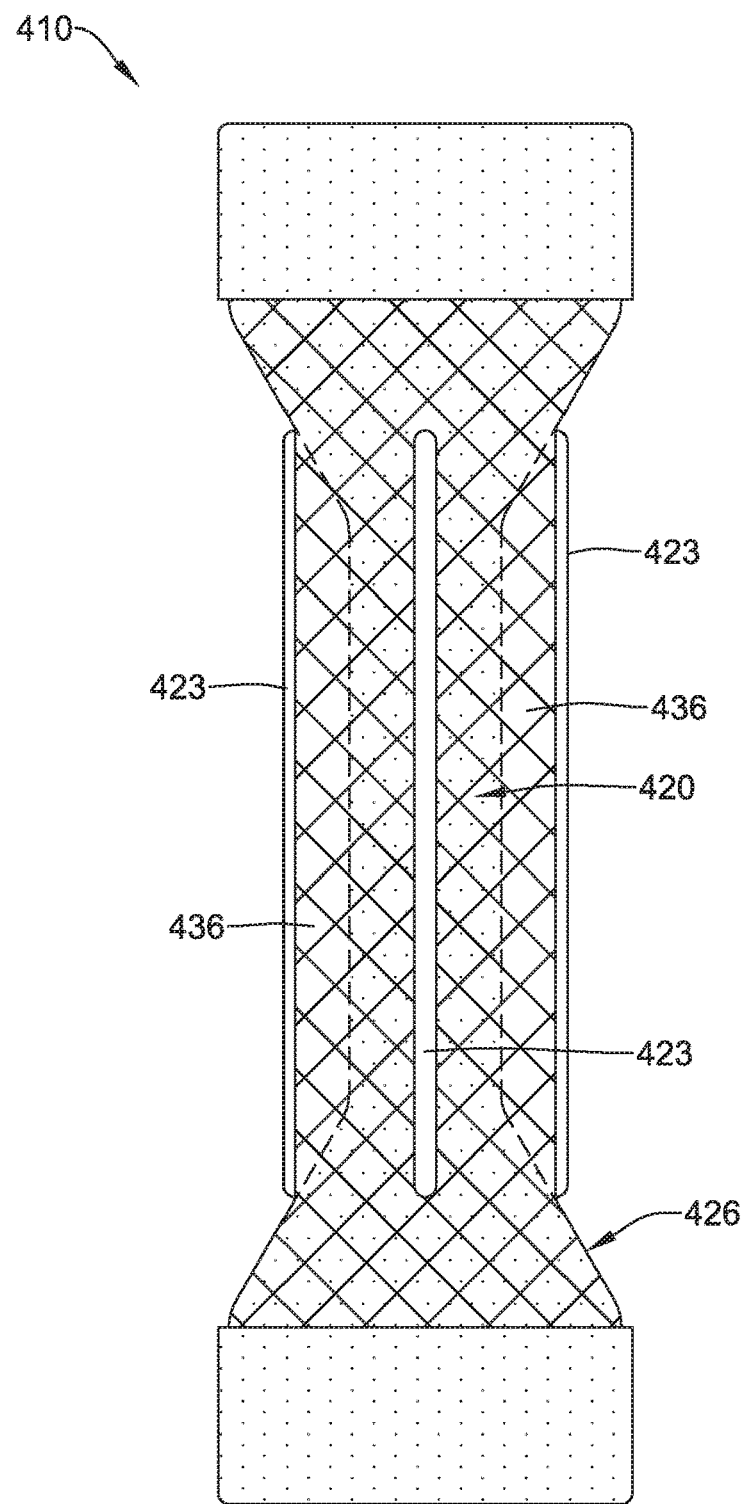
FIG. 8A is a plan view of another example stent including a liner and covered portions.

FIG. 8A shows an example stent 410. Example stent 410 that may be similar in form and function to the stent designs disclosed above. However, as FIG. 8A illustrates, stent 410 includes additional outer layers 423 disposed along the outer surface 426 of stent 410. FIG. 8A shows outer layers 423 may be positioned such that they extend longitudinally along the outer surface 426 of stent 410. As shown in FIG. 8A, individual outer layers 423 may be circumferentially spaced apart from one another. It can be appreciated that the configuration of outer layers 423 creates one or more tissue ingrowth regions 436 (similar to in function to those described above) along the stent 410. Tissue ingrowth regions 436 may be uncovered portions of the tubular scaffold of stent 410. Inner layer 420 may be located radially inward of tissue ingrowth regions 436 to limit the amount a tissue ingrowth permitted.

Figure 8B:
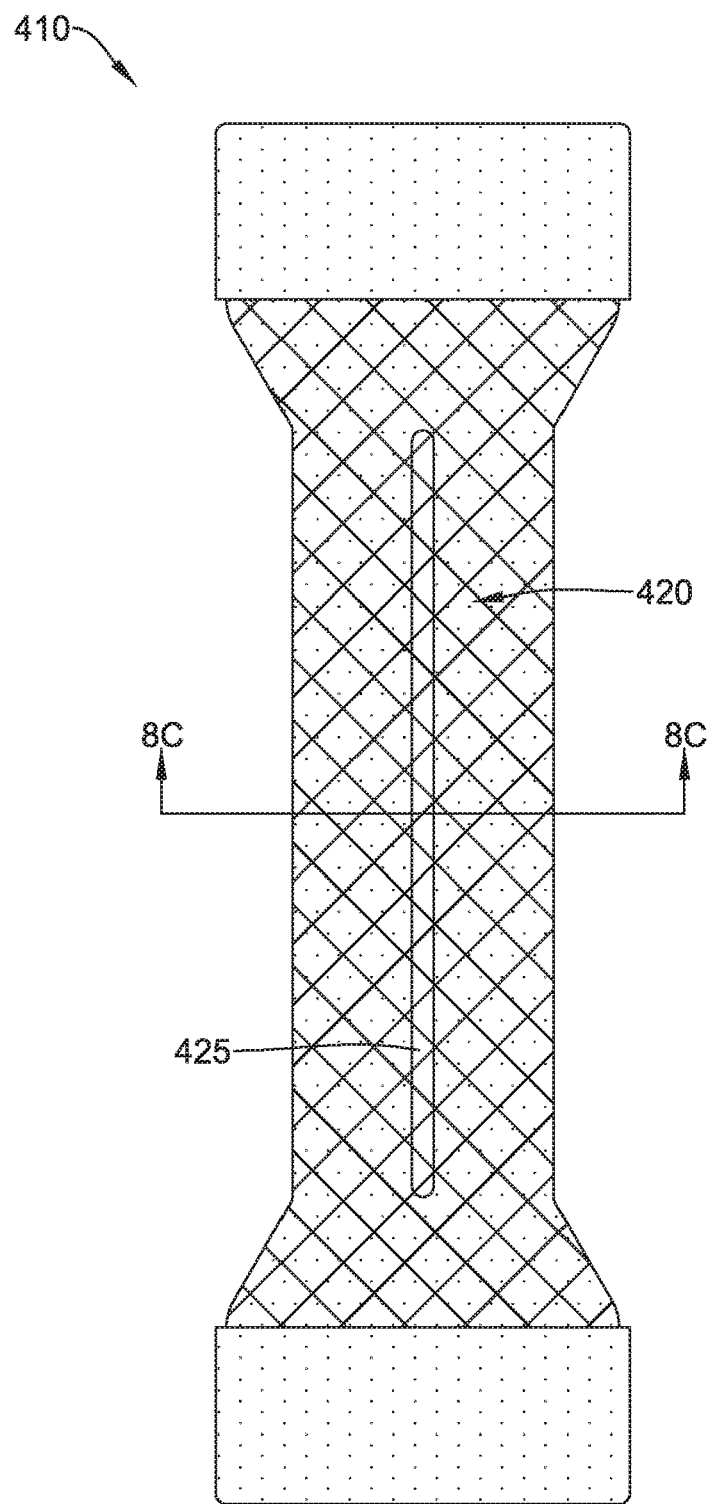
FIG. 8B is a plan view of another example stent including a liner.
Figure 8C:
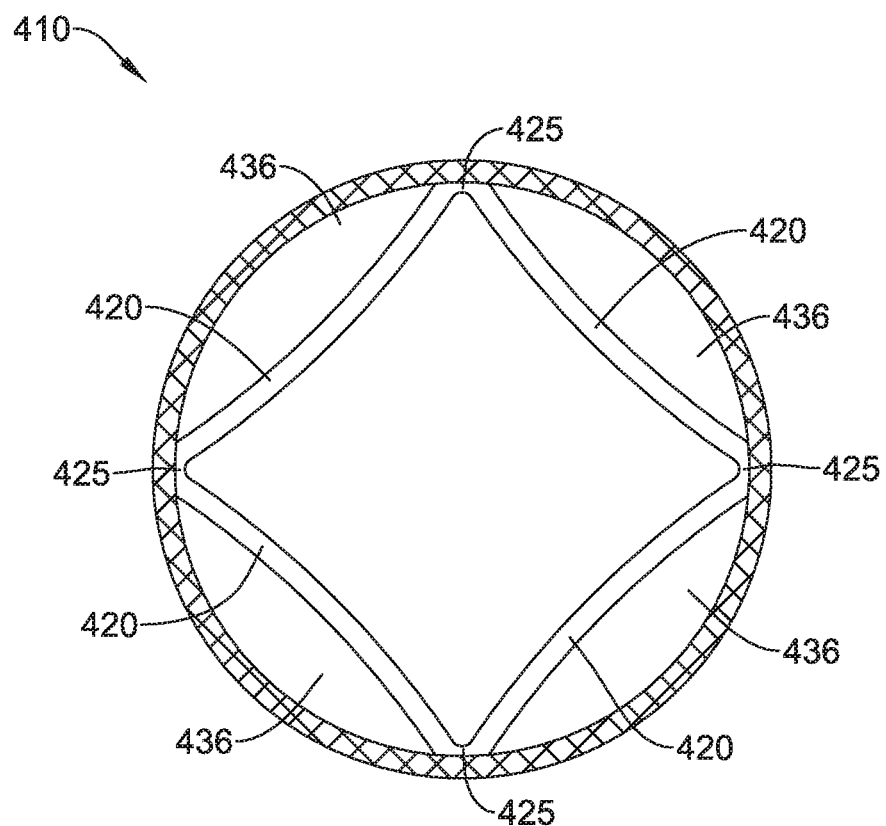
FIG. 8C is a cross-sectional view of another example stent.

Alternatively, some stent examples disclosed herein may be designed such that one or more portions of an inner layer extending along the inner surface of the stent may be spaced away from (i.e., spaced radially inward of) the inner surface of the stent, providing a gap or space therebetween. FIG. 8B illustrates an alternative stent example (which may be similar in form and function to the stent design disclosed above with respect to FIG. 8A) having an inner layer 420 spaced away from an inner surface of stent 410. As shown in FIG. 8B and FIG. 8C (discussed below), inner layer 420 may include one or more discrete attachment points 425 along the inner surface of stent 410 in which the inner layer 420 is attached to the inner surface of stent 410. It should be noted that the discrete attachment points of inner layer 420 may extend the full (or partial) longitudinal length (e.g., from the distal end region to the proximal end region) along the inner surface of stent 410.

FIG. 8C illustrates an example cross-section along line 8C-8C of example stent 410 shown in FIG. 8B. FIG. 8C illustrates that one or more portions of inner layer 420 may be attached along the inner surface of stent 410. Further, the inner layer 420 may be attached along the inner surface of stent 410 at one or more discrete attachment points 425. It can be appreciated that the space between the discrete attachment points 425 may create one or more tissue ingrowth regions 436.

Example stents disclosed herein may include one or more anchoring members designed to prevent the tubular member from shifting with respect to a body lumen in which the stent member is implanted. For example, some stents disclosed herein may include anti-migration elements. Anti-migration elements may include hooks, barbs, posts, flares, hoops, fins, quills, tines or the like. Anti-migration features may be beneficial in controlling the amount that a stent moves during and/or after deployment in the body lumen.

As discussed above, while medical device 10 is implanted along a body lumen, tissue ingrowth may occur along the tissue ingrowth region, which may reduce migration of implantable medical device 10 within the body lumen. However, in some examples, it may be necessary to remove medical device 10 from the body lumen. In at least some examples contemplated herein, removal of medical device 10 (which is effectively anchored to the body lumen via tissue ingrowth) may include positioning a second medical device (e.g., a second expandable stent) within the lumen of the medical device 10 such the second medical device may exert a radially outward force along the tissue ingrowth region, thereby causing the ingrown tissue to recede. In other words, a second expandable stent may be deployed within the lumen of medical device 10, whereby the radial outward expansion of the second stent "pushes back" the ingrown tissue, causing it to recede radially outward (toward the vessel wall) and thereby reducing the force necessary to remove medical device 10 and/or the second stent. This method of using a second medical device to remove medical device 10 (e.g., the anchored stent) will be further illustrated and described below.

Figure 9:
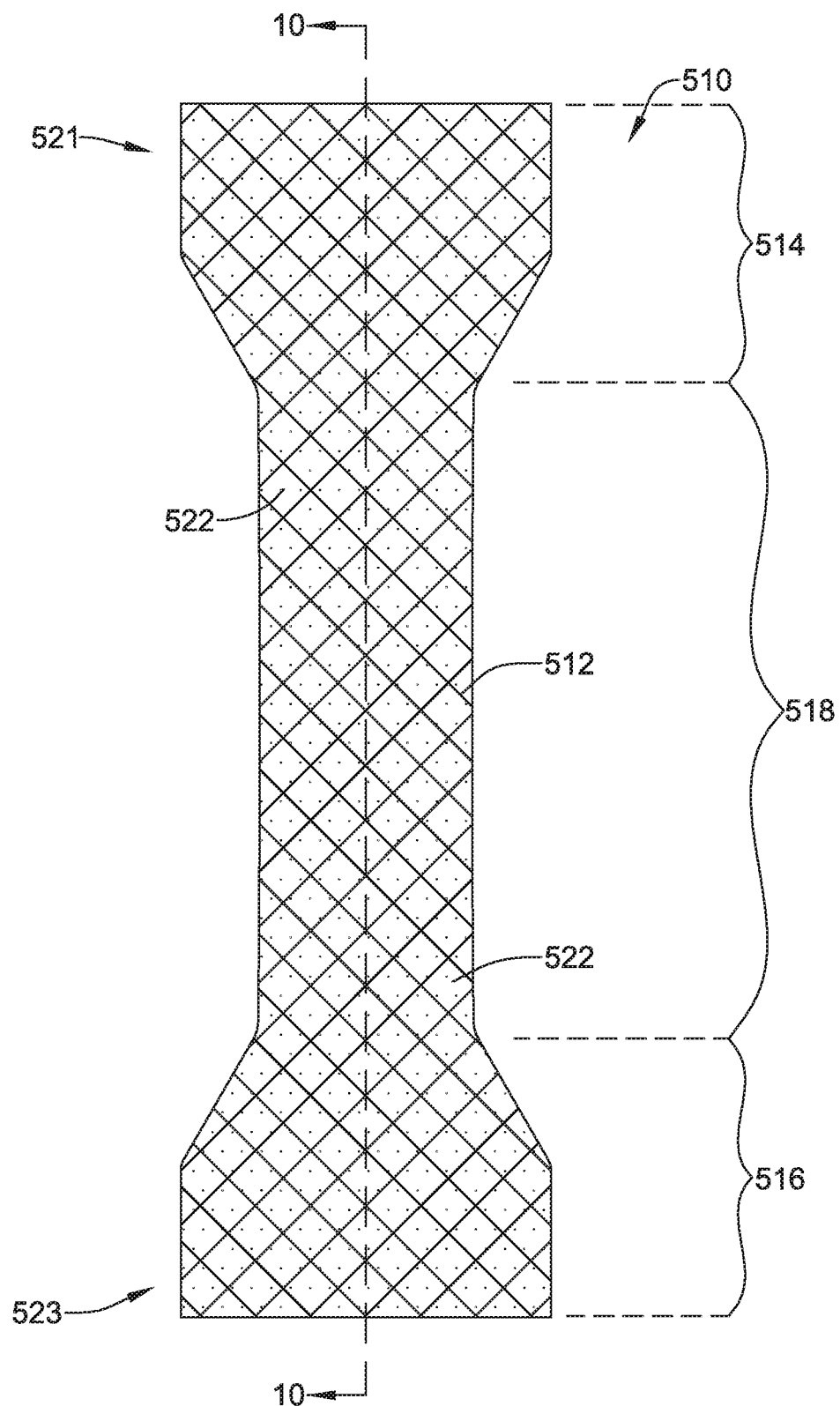
FIG. 9 is another example stent.

FIG. 9 shows an example second stent 510. In some instances, second stent 510 may be referred to as an interior stent, removal stent and/or retrieval stent 510 configured to by positioned within a lumen of a previously implanted stent. Stent 510 may have a first end 521, an opposite second end 523 and a lumen extending therein. When positioned in a body lumen (e.g., esophagus) the first or proximal end 521 may be defined as the end of stent 510 closest to a patient's mouth and the second or distal end 523 may be defined as the end of stent 510 closest to a patient's stomach.

Additionally, stent 510 may include one or more stent strut members 512 forming a tubular scaffold. Stent strut members 512 may extend helically, longitudinally, circumferentially, or otherwise along stent 510. While FIG. 9 shows stent strut members 512 extending along the entire length of stent 510, in other examples, the stent strut members 512 may extend only along a portion of stent 510. In some instances, stent struts 512 may be wires or filaments which are braided, wrapped, intertwined, interwoven, weaved, knitted, loops (e.g., bobbinet-style) or the like to form the stent structure. In other instances, the stent struts 512 may be portions of a monolithic structure formed from a cylindrical tubular member, such as a laser-cut Nitinol tube.

Additionally, FIG. 9 shows example stent 510 including a first flared end region 514 proximate the first end 521 and/or a second flared end region 516 proximate the second end 523 of stent 510. In some instances, first flared region 514 and second flared region 516 may be defined as an increase in the outer diameter, the inner diameter or both the inner and outer diameters along one or both of the first end 521 and/or second end 523 of stent 510. Further, FIG. 9 illustrates stent 510 including a medial region 518 positioned between first flared region 514 and second flared region 516.

However, it is contemplated that while FIG. 9 shows stent 510 including both a first flared region 514 and a second flared region 516, stent 510 may only include one flared region. For example, it is contemplated that stent 510 may include only flared region 514 or flared region 516. It is further contemplated that all or a portion of first flared region 514 and/or second flared region 516 may flare outwardly (e.g., away from the central, longitudinal axis of stent 510). Alternatively, it is further contemplated that all or a portion of first flared region 514 and/or second flared region 516 may flare inwardly (e.g., toward the central, longitudinal axis of stent 510).

In some instances, stent 510 may be a self-expanding stent or stent 510 may be a balloon expandable stent. Self-expanding stent examples may include stents having one or more struts 512 combined to form a rigid and/or semi-rigid stent structure. For example, stent struts 512 may be wires or filaments which are braided, wrapped, intertwined, interwoven, weaved, knitted, looped (e.g., bobbinet-style) and combinations thereof to form the stent structure. For example, while the example stents disclosed herein may resemble a braided stent, this is not intended to limit the possible stent configurations. Rather, the stents depicted in the Figures may be stents that are knitted, braided, wrapped, intertwined, interwoven, weaved, looped (e.g., bobbinet-style) or the like to form the stent structure. Alternatively, stent 510 may be a monolithic structure formed from a cylindrical tubular member, such as a single, cylindrical tubular laser-cut Nitinol tubular member, in which the remaining portions of the tubular member form the stent struts 512. Openings or interstices through the wall of the stent 510 may be defined between adjacent stent struts 512.

Stent 510 in examples disclosed herein may be constructed from a variety of materials. For example, stent 510 (e.g., self-expanding or balloon expandable) may be constructed from a metal (e.g., Nitinol, Elgiloy, etc.). In other instances, stent 510 may be constructed from a polymeric material (e.g., PET). In yet other instances, stent 510 may be constructed from a combination of metallic and polymeric materials. Additionally, stent 510 may include a bioabsorbable and/or biodegradable material.

In some instances, example stent 510 may include one or more layers (e.g., coverings) positioned on and/or adjacent to the inner and/or outer surface of the tubular scaffold of stent 510. For example, FIG. 9 shows example stent 510 including an outer layer 522 (depicted as a dotted pattern in FIG. 9) disposed along at least a portion of the outer surface of stent 510 (e.g., along the middle portion, along the first flared portion 514 and/or the second flared portion 516 of stent 510). In some instances, the outer layer 522 may cover the entire outer surface of the tubular scaffold of stent 510. In some instances, outer layer 522 may be an elastomeric or non-elastomeric material. For example, outer layer 522 may be a polymeric material, such as silicone, polyurethane, or the like.

Additionally, example stent 510 may include one or more layers positioned on and/or adjacent to the inner surface of stent 510. For example, stent 510 may include an inner layer (not shown in the Figures) disposed within the lumen of stent 510. In some instances, inner layer may be an elastomeric or non-elastomeric material. For example, inner layer may be a polymeric material, such as silicone, polyurethane, UE, PVDF, Chronoflex® or similar biocompatible polymeric formulations.

Figure 10:
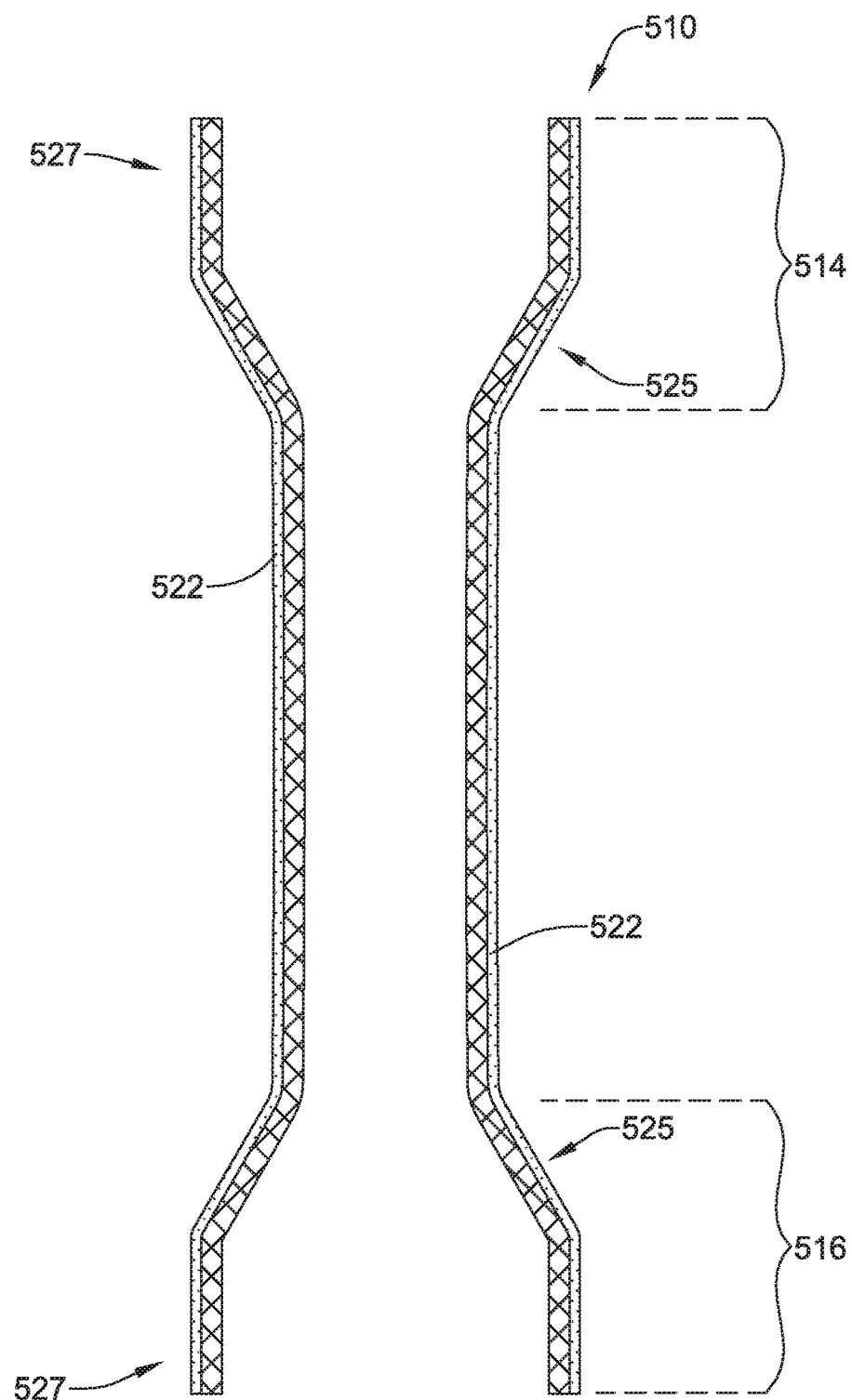
FIG. 10 is a cross-sectional view of the stent of FIG. 9 taken along line 10-10 of FIG. 9.

FIG. 10 shows a cross-section of example stent 510 along line 10-10 of FIG. 9. FIG. 10 illustrates that first flared region 514 and/or second flared region 516 may include tapered portion 525 and end portion 527. While FIG. 10 shows tapered portions tapering radially outward toward ends of stent 510, it is contemplated that one or more of tapered portions 525 may, alternatively, taper radially inward.

As discussed above, FIG. 10 illustrates stent 510 may include an outer layer 522 disposed along an outer surface of stent 510. For example, in some instances, stent 510 may include an outer layer 522 disposed along the outer surface of a middle portion between flared ends 514, 516, one or more of both tapered portions 525 and/or end portions 527. Further, in some examples, outer layer 522 may extend longitudinally along the entire length and circumferentially around the entire circumference of outer surface of stent 510.

Figure 11:
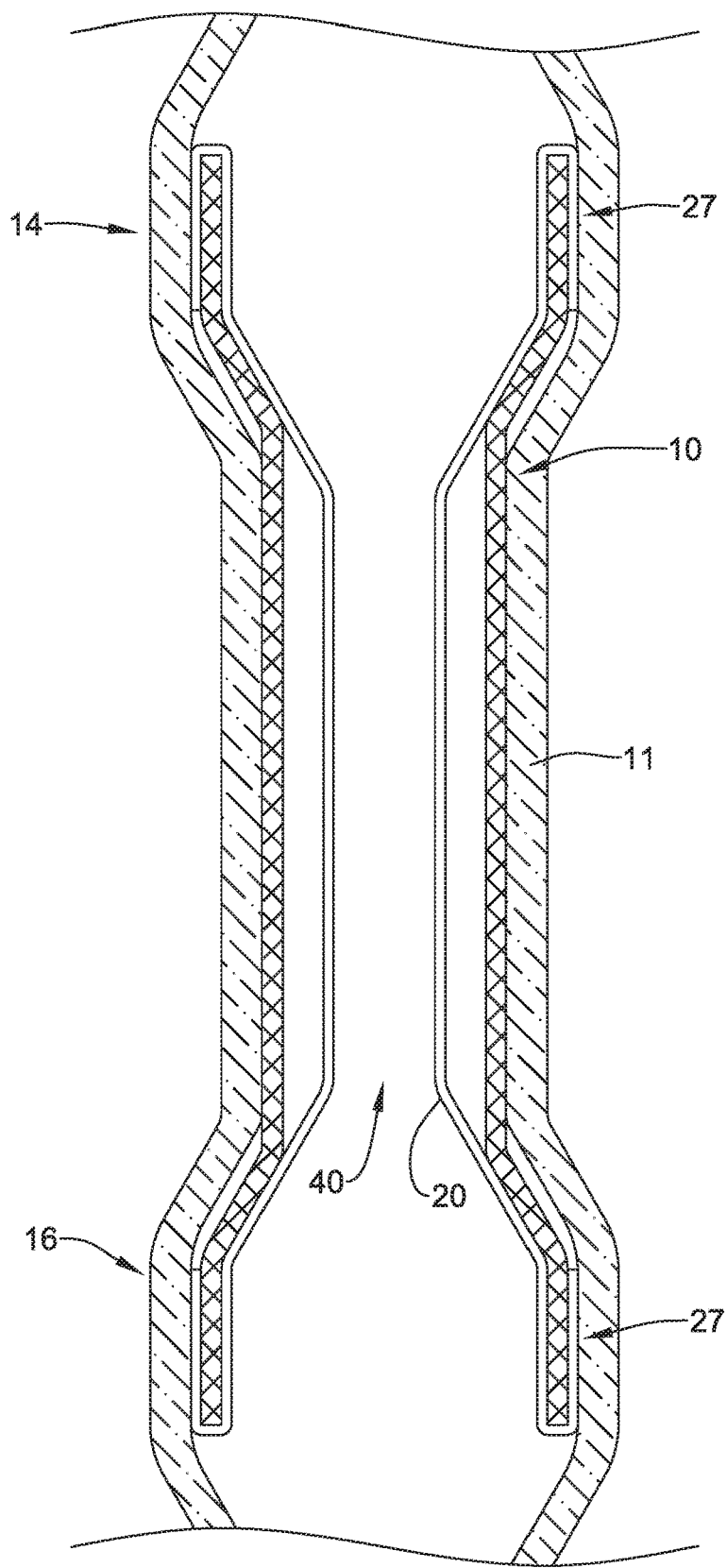
FIGS. 11-13 illustrate an example stent positioned in a body lumen undergoing a hyperplastic response.
Figure 12:
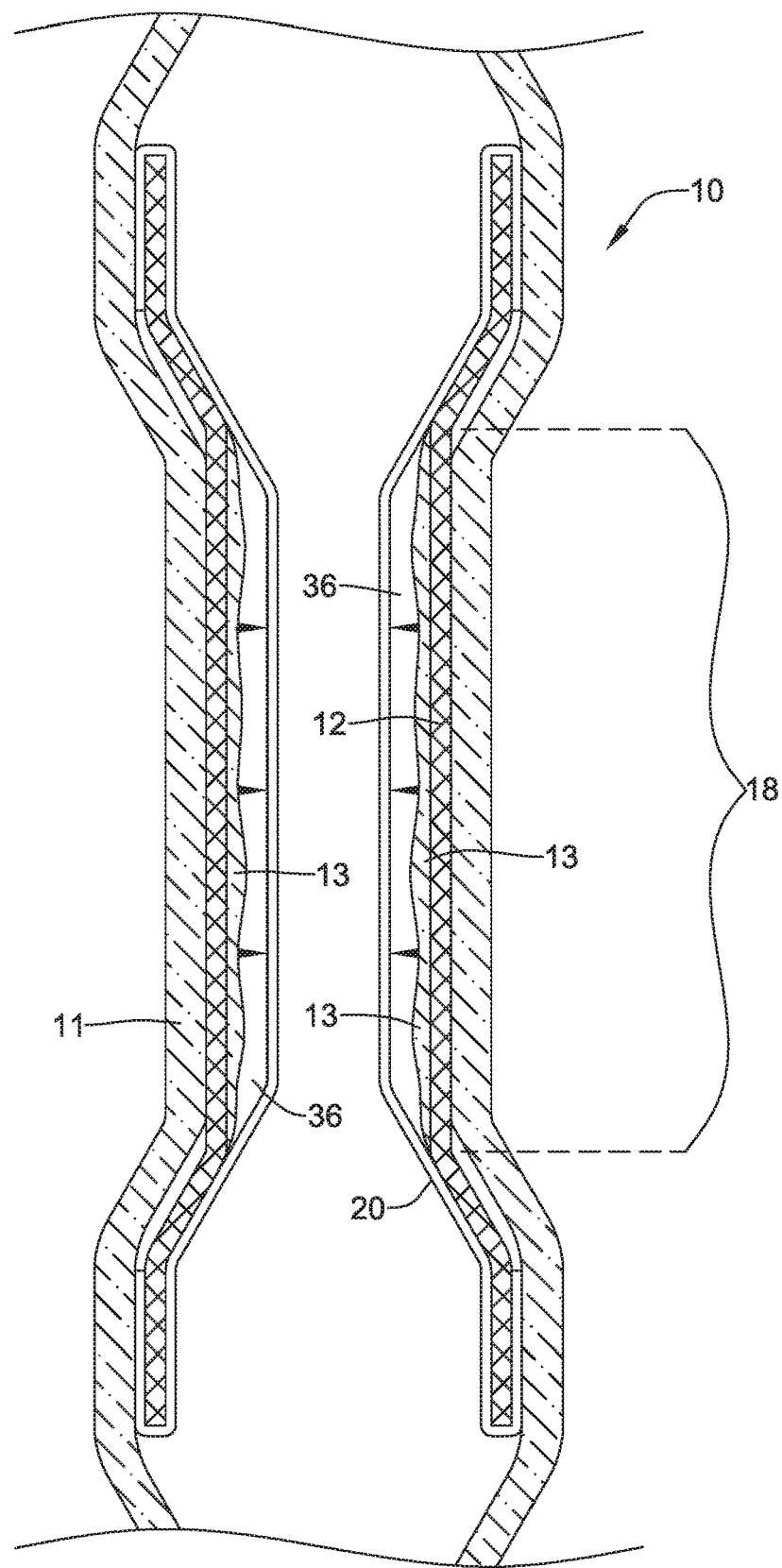
Figure 13:
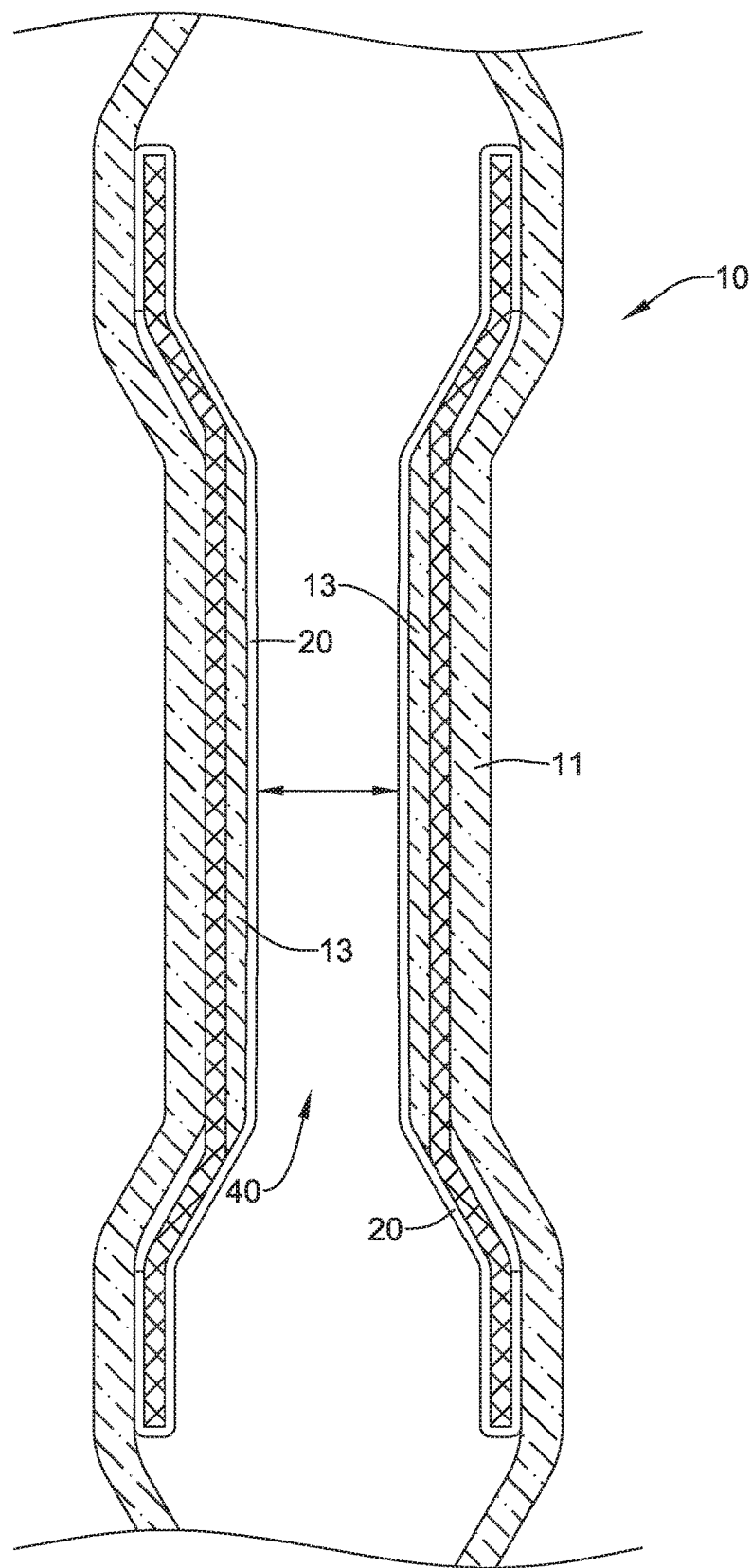
Figure 16:
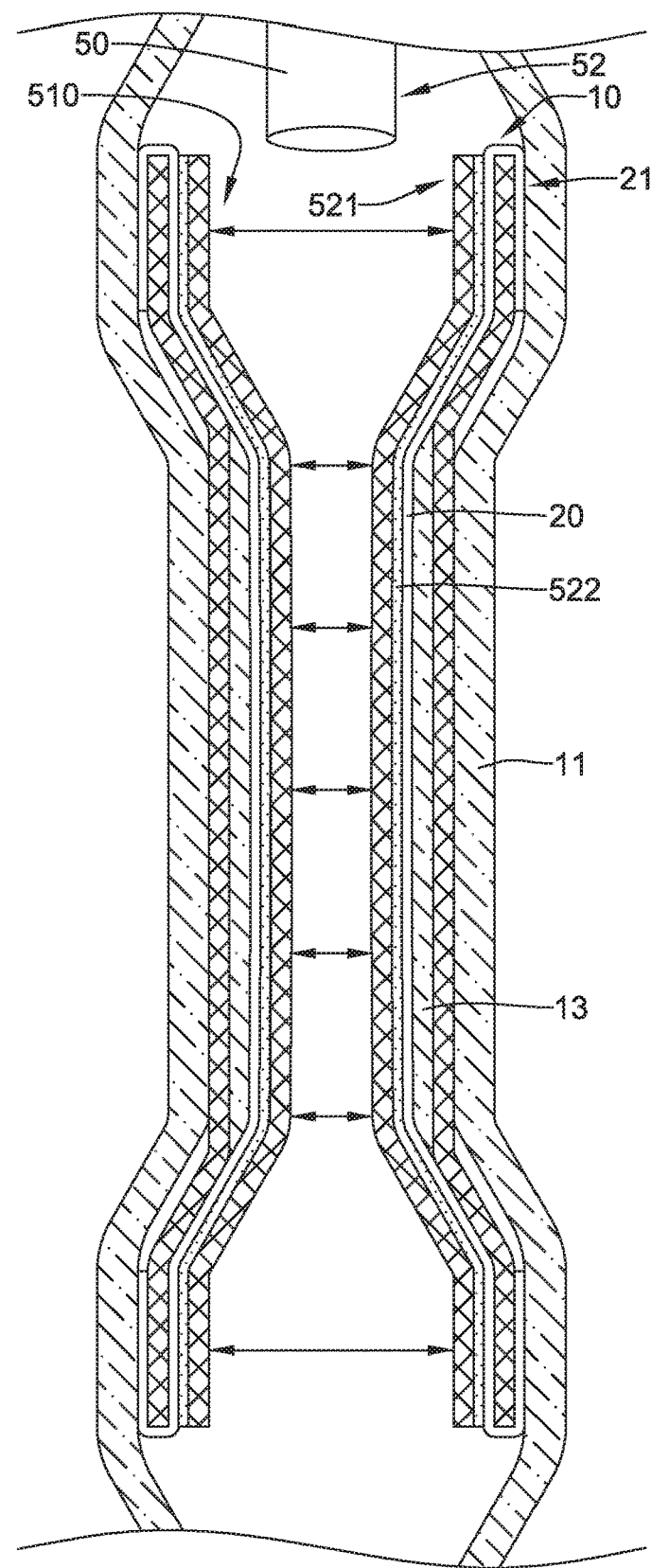
Figure 17:
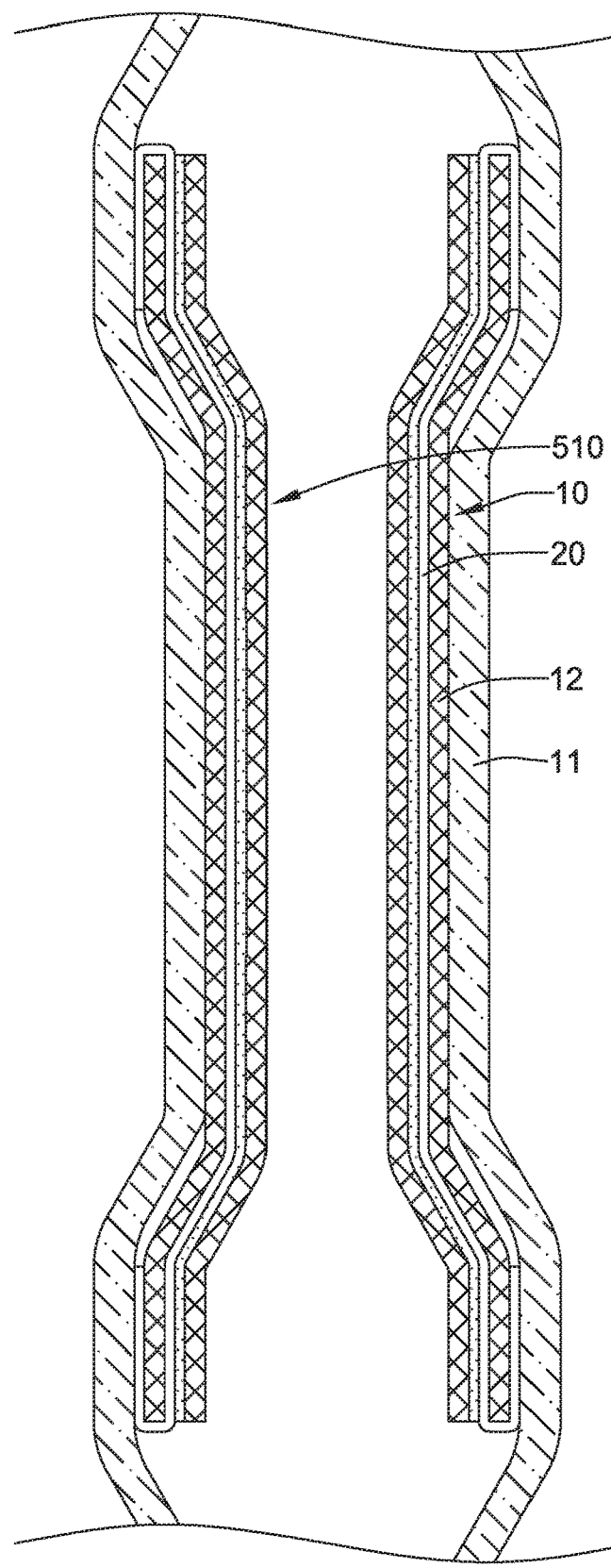
Figure 18:
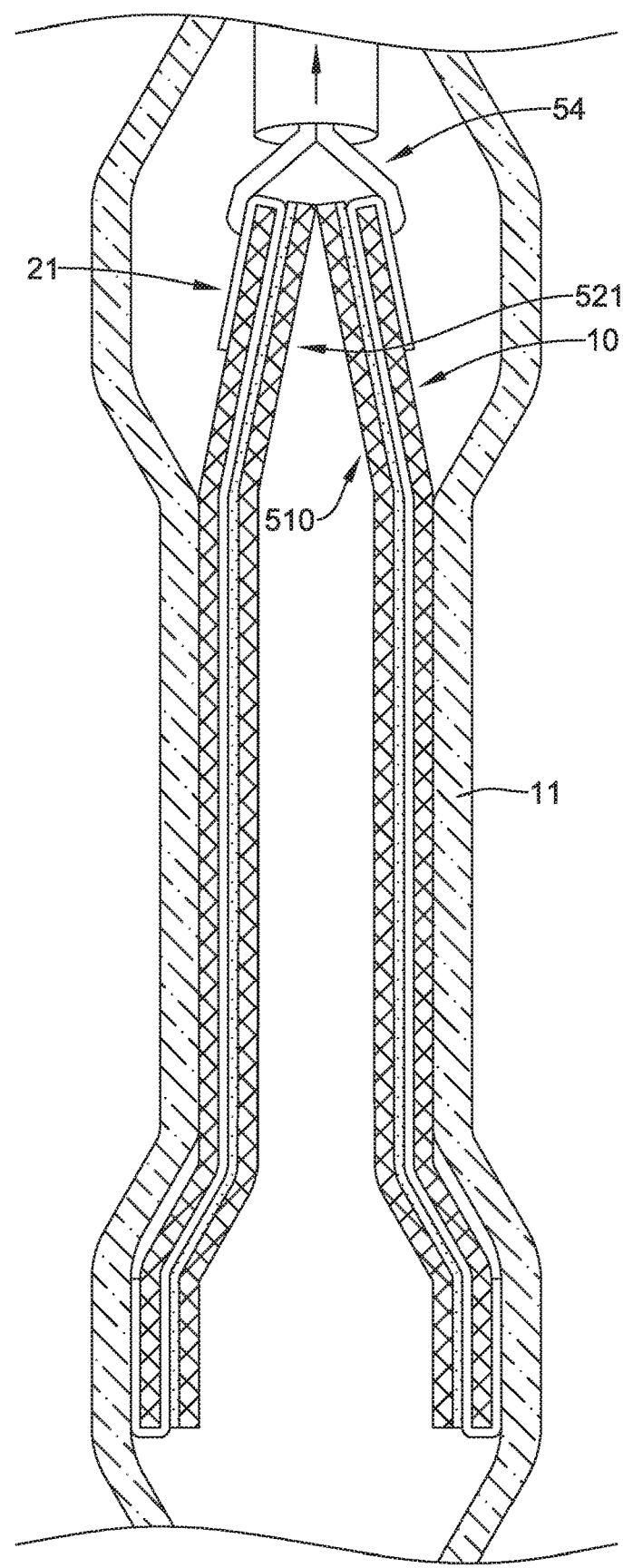
FIG. 18 illustrates the retrieval of the example stent system illustrated in FIGS. 14-17.

As will be discussed in greater detail below, FIGS. 11-13 illustrate an example stent 10 undergoing a hyperplastic response, FIGS. 14-17 illustrate the deployment and positioning of an example retrieval stent within stent 10 and FIG. 18 illustrates the removal of both stent 10 and the retrieval stent 510.

FIGS. 11-13 illustrate an example stent undergoing a hyperplastic response of tissue within an example body lumen subsequent to implantation of stent 10 within a body lumen 11. FIG. 11 shows example stent 10 deployed in body lumen 11. As illustrated, upon initial deployment in the body lumen 11, the end portion 27 of the first flared region 14 and the end portion 27 of the second flared region 16 may apply a radially outward force upon the inner surface of body lumen 11 as the expandable scaffold of stent 10 expands to an expanded state in the body lumen 11. This radially outward force exerted on the inner surface of body lumen 11 may provide a temporary resistance to migration of stent 10 within the body lumen 11.

Additionally, the end portions 27 of stent 10 may contact the tissue on the inner surface of body lumen 11. This contact of the end portions 27 with the tissue of the inner surface of the body lumen 11 may provide a seal that funnels food or other material through lumen 40 of stent 10. For example, as food or other material travels down the esophagus, the flared portions 14/16 of stent 10 may prevent the food from traveling along the exterior of stent 10 and along the inner surface of body lumen 11. Rather, flared portions 14/16 are designed to provide a circumferential seal around the inner surface of body lumen 11 such that the food is directed through the lumen 40 of stent 10. As discussed above, the inner layer 20 of stent 10 may create a passageway (e.g., lumen 40) through which food and other material may travel (without leaking to the outer surface of stent 10).

Over time, tissue may grow through interstices of the stent scaffold along medical region 18. FIG. 12 illustrates tissue 13 extending through interstices of the stent filaments 12 along the medial region 18 of stent member 10 radially inward of the uncovered portion of the tubular scaffold of stent 10. FIG. 12 further illustrates that the tissue 13 is growing into the tissue ingrowth region 36 toward liner 20 (as depicted by the arrows in FIG. 12). Thus, tissue may grow through interstices of the tubular scaffold of stent 10 and around struts or filaments 12 of tubular scaffold of stent 10 throughout the uncovered portion of medial region 18.

Inner layer 20 may limit the amount of tissue in-growth permitted. FIG. 13 illustrates that tissue 13 has grown radially inward from the wall of example body lumen 11 to a position in which it has contacted inner layer 20 radially inward. However, as shown in FIG. 13, inner layer 20 has reached a point at which it will no longer deflect radially inward, and therefore prevents tissue 13 from further collapsing lumen 40 of stent member 10 (as depicted by the double-ended arrow in FIG. 13). Thus, inner layer 20 may be configured to maintain a desired lumen diameter through stent 10 while stent 10 is implanted in a patient.

In some instances, it may be desirable to remove stent 10 subsequent tissue in-growth through interstices of the tubular scaffold. However, the tissue-ingrowth may hinder removal and/or cause undesirable trauma to the body lumen. As discussed above, FIGS. 14-18 illustrate an example methodology for retrieving and/or removing an example stent 10 (or any other devices disclosed herein) from a body lumen (e.g., the esophagus) while reducing the amount of trauma to the body lumen. Example stent 10 shown in FIGS. 14-18 may depict stent 10 illustrated and described with respect to FIGS. 11-13. However, stent 10 described in the following methodology may also be similar in form and function to stent 10 of FIGS. 1 and 2 discussed above. Further, while the following figures describe example stent 10 being retrieved and/or removed from the esophagus, it is contemplated that the methodology may be used to retrieve and/or remove stent 10 (or any other devices disclosed herein) from any other body lumen.

Figure 14:
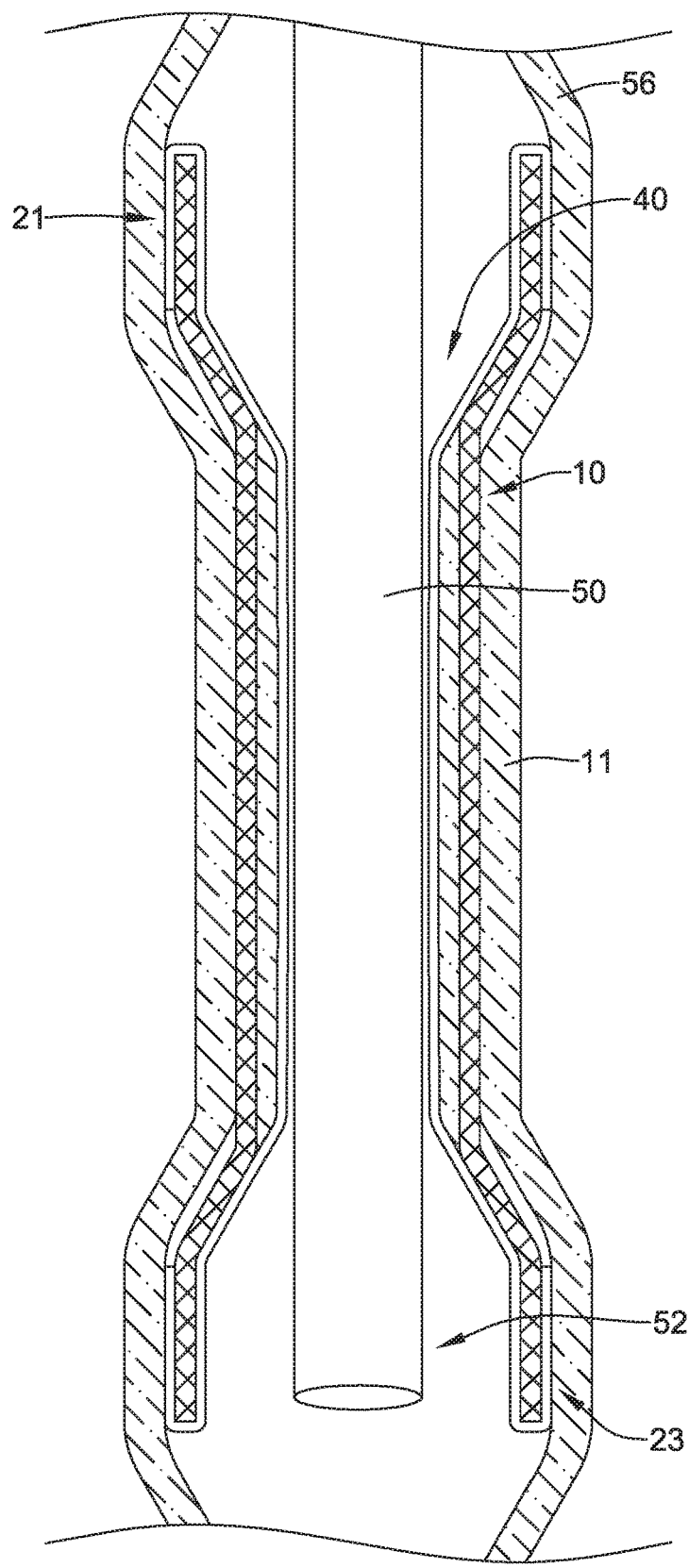
FIGS. 14-17 illustrate an example method for deploying an example stent within another example stent.

FIG. 14 shows an example first step in removing stent 10 from body lumen 11. Specifically, delivery device 50 may be advanced through body lumen 11 to a first end 21 of stent 10. The end portion 52 of delivery device 50 may then be further advanced through the lumen 40 of the stent 10 such that the end portion 52 is positioned adjacent the second end 23 of the stent 10.

Figure 15:
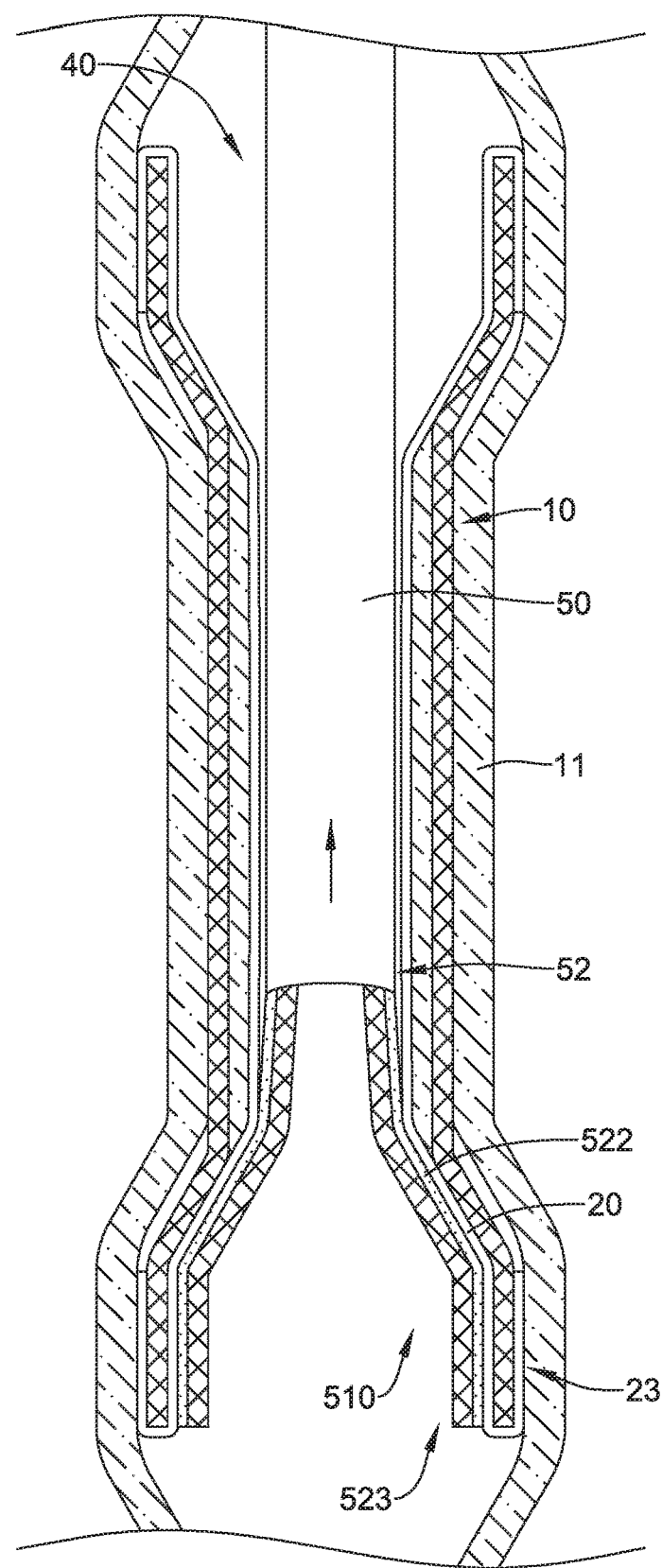

FIG. 15 illustrates an example second step in removing stent 10 from body lumen 11. Specifically, FIG. 15 illustrates that a clinician may retract the end portion 52 of the delivery device 50 in a proximal direction depicted by the arrow in FIG. 15. Specifically, the delivery device 50 (e.g., an outer sheath of delivery device 50) may be retracted in a distal-to-proximal direction within lumen 40 of the stent 10. In other words, the delivery device may be retracted from second end 23 toward the opposite end of the stent 10. FIG. 15 further illustrates that as the delivery device 50 is retracted, the second end 523 of secondary stent 510 (e.g., retrieval stent) is deployed with the lumen 40 of stent 10. Additionally, it can be appreciated that as retrieval stent 510 is deployed, it radially expands such that the outer covering 522 of the second end 523 of stent 510 contacts the inner liner 20 of stent 10. Further, as illustrated in FIG. 15, it may be desirable that the second end 523 of retrieval stent 510 and the second end 23 of stent 10 be substantially aligned longitudinally along body lumen 11.

FIG. 16 illustrates an example third step in removing stent 10 from body lumen 11. Specifically, FIG. 16 illustrates that delivery device 50 may be fully retracted to a position in which retrieval stent 510 has been fully deployed from the end portion 52 of the delivery device 50. Additionally, it can be appreciated that after retrieval stent 510 is fully deployed from delivery device 50, it expands radially outward such that the outer covering 522 of stent 510 contacts the inner liner 20 of stent 10 throughout the length of stent 10, with the expandable scaffold of stent 510 exerting a radially outward force on inner liner 20 of stent 10. For example, the expandable scaffold of stent 510 can exert a radially outward force throughout the medial region 18 of the inner liner 20.

Further, as illustrated in FIG. 16, it may be desirable that the first end 521 of retrieval stent 510 and the first end 21 of stent 10 may be substantially aligned longitudinally along the body lumen 11. Further, FIG. 16 illustrates that in some instances it may be desirable that both the first and second ends of retrieval stent 510 substantially align with the first and second ends of stent 10.

Additionally, it can be appreciated that in some instances the retrieval stent 510 may include a profile along its outer surface that matches the profile of the inner surface of stent 10. In other words, in some instances it may be desirable for stent 10 and retrieval stent 510 to have a similar, or substantially equivalent geometric shape. It can further be appreciated that if the profile of retrieval stent 510 matches the profile of stent 10, the retrieval stent 510, when deployed within the lumen 40 of stent 10, may contact substantially the entire inner surface of stent 10.

As discussed above, FIG. 16 further illustrates that when retrieval stent 510 is positioned and deployed within the lumen 40 of stent 10, it may exert a radially outward force (depicted by the double-ended arrows in FIG. 16) that pushes outward against the inner surface of stent 10. For, example, retrieval stent 510 may be configured to have a deployed, radially expanded outer diameter greater than the inner diameter of the medial region 18 of stent 10 to exert a radial outward force against inner liner 20. Accordingly, this outward radial force may push the portion of liner 20 that is adjacent the tissue ingrowth region, thereby exerting an outward radial force against the tissue 13, as shown in FIG. 16. It can be appreciated that stent 510 may be designed such that it exerts an outward radial force which is large enough to push both liner 20 and tissue 13 radially outward toward body lumen 11, thereby causing tissue 13 to retreat and effectively die off. In some examples, the outward radial force exerted by stent 510 may be about 0.10 N to about 2.5 N, or about 0.15 N to about 2.0 N. In some instance, the outward radial force exerted by stent 510 may be about 0.10 N or more, about 0.15 N or more, about 0.5 N or more, about 1.0 N or more, about 1.5 N or more, or about 2.0 N or more.

FIG. 17 illustrates stent 10 and retrieval stent 510 of FIG. 16 after the retrieval stent 510 has been deployed within stent 10 and allowed to exert an outward radial force along the tissue ingrowth region of liner 20. As can appreciated from FIG. 17, the tissue 13 present in FIG. 16 has effectively died off and liner 20 has relaxed to a position in which it is positioned along the inner surface of the tubular scaffold of stent 10 throughout medial region 18. As discussed above, because the retrieval stent 510 has reduced the amount of tissue 13 extending through the stent struts 12 of stent 10, tissue 13 no longer attaches stent 10 to the inner surface of body lumen 11 with as much force as when the tissue 13 is fully ingrown into the stent struts 12. Accordingly, this reduced attachment force translates into a lower force which is necessary to remove stent 10 and/or stent 510 from body lumen 11.

FIG. 18 illustrates an example step in removing stent 10 from body lumen 11. Removal of the stent 10 may be performed once tissue in-growth into the interstices of the tubular scaffold of stent 10 has sufficiently receded. For example, removal of stent 10 may be performed approximately 7-14 days after placing retrieval stent 510 within stent 10. In some instances, removal of stent 10 may be performed within 1 week or less, within 2 weeks or less, or within 3 weeks or less after placing retrieval stent 510 within stent 10. Specifically, FIG. 18 illustrates that a clinician may utilize a retrieval device 54 (e.g., forceps, clamp, etc.) to remove both stent 10 and/or retrieval stent 510. As illustrated in FIG. 18, the retrieval device 54 map grasp the first end portions 21/521 of stent 10 and retrieval stent 510 and pull them in a direction out of the body (indicated by the arrow in FIG. 18). The force exerted by the retrieval device 54 may be sufficient to remove both the stent 10 and retrieval stent 510 from the inner surface of the body lumen 11 without damaging the inner surface of the body lumen 11. Alternatively, retrieval device 54 may grasp or hook a retrieval suture extending circumferentially around the end of stent 10. When pulled proximally, the retrieval suture may collapse the proximal end of stent 10 and/or the proximal end of stent 510 to facilitate withdrawal of the stents 10, 510. Accordingly, stents 10, 510 may be removed from the body lumen 11 simultaneously. Alternatively, stents 10, 510 may be removed from the body lumen sequentially, if desired.

The materials that can be used for the various components of stent 10 and stent 510 (and/or other stents disclosed herein) and the various medical devices disclosed herein may include those commonly associated with medical devices. For simplicity purposes, the following discussion makes reference to stent 10 and stent 510 and other components of stent 10 and stent 510. However, this is not intended to limit the devices and methods described herein, as the discussion may be applied to other similar medical devices disclosed herein.

Stent 10 and stent 510 and other components of stent 10 and stent 510 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of stents 10, 510 and other components of stent 10 and stent 510 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of stent 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of guidewire 10 to achieve the same result.

In some embodiments, a degree of Magnetic Resonance Imaging (MRI) compatibility is imparted into stent 10. For example, stents 10, 510 and other components of stent 10 and stent 510, or portions thereof, may be made of a material that does not substantially distort the image and create substantial artifacts (e.g., gaps in the image). Stent 10 and stent 510 and other components of stent 10 and stent 510, or portions thereof, may also be made from a material that the Mill machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:
1. A system for treating a body lumen, comprising:
   a first stent including:
      a first tubular scaffold, the first tubular scaffold including an inner surface, an outer surface and a lumen extending therethrough; and
      a liner disposed within the lumen of the first tubular scaffold, wherein the liner is configured to be radially spaced from the inner surface of the first tubular scaffold to permit tissue ingrowth along a portion of first tubular scaffold; and
   a second stent including:
      a second tubular scaffold and a covering disposed on the second tubular scaffold;

wherein the second stent is configured to be positioned within the first stent such that expansion of the second stent causes the tissue ingrowth to recede.

2. The system of claim 1, wherein the second tubular scaffold is configured to expand radially outward, and wherein the radially outward expansion of the second tubular scaffold causes the tissue ingrowth to recede.

3. The system of claim 1, wherein the first stent includes an inner surface having a first profile, and wherein the second stent includes an outer surface having a second profile, and wherein the first profile matches the second profile.

4. The system of claim 1, wherein the second stent includes a first end region and a second end region, and wherein the first end region, the second end region, or both the first and second end regions have a flared portion.

5. The system of claim 1, wherein the liner is configured to be radially spaced from a medial region of the first tubular scaffold to permit a tissue ingrowth region along the medial region, and wherein the second stent is configured to exert a radially outward expansion force along the tissue ingrowth region, wherein the radially outward expansion force is sufficient to cause the tissue ingrowth to recede.

6. The system of claim 5, wherein the radially outward expansion force is 0.15 N or more.

7. The system of claim 5, wherein the liner is configured to limit the amount of tissue ingrowth into the medial region of the tubular scaffold due to a hyperplastic response.

8. The system of claim 5, wherein the tissue ingrowth region is formed between the inner surface of the tubular scaffold and an outwardly-facing surface of the liner.

9. The system of claim 5, wherein the portion of the liner extending along the tissue ingrowth region is configured to deflect radially inward from the inner surface of the tubular scaffold.

10. The system of claim 9, wherein the medial portion of the tubular scaffold includes a first inner diameter, and wherein the diameter of the liner along the tissue ingrowth region includes a second inner diameter, and wherein the second inner diameter is greater than 25% of the diameter of the first inner diameter.

11. The system of claim 5, wherein the tissue ingrowth region extends circumferentially around the inner surface of the tubular scaffold.

12. The system of claim 5, wherein a medial region of the tubular scaffold of the second stent has an outer diameter in a radially expanded state of the second stent greater than an inner diameter along a medial region of the tubular scaffold of the first stent in a radially expanded state of the first stent.

13. A system for treating the esophagus, comprising:
a first stent including:
a first expandable scaffold, the first expandable tubular scaffold including an inner surface, an outer surface and a lumen extending therein; and
a liner disposed within the lumen of the first expandable scaffold, wherein the liner is configured to be radially spaced from a medial region of the first expandable scaffold to define a tissue ingrowth region along a portion of first expandable scaffold; and
a second stent including:
a second expandable scaffold and a covering disposed on the second expandable scaffold;
wherein the second stent is configured to be positioned within the first stent such that expansion of the second stent causes the tissue ingrowth to recede along the tissue ingrowth region.

14. The system of claim 13, wherein the second expandable scaffold is configured to expand radially outward, and wherein the radially outward expansion of the second expandable scaffold causes the tissue ingrowth to recede.

15. The system of claim 13, wherein the second stent is configured to exert a radially outward expansion force along the tissue ingrowth region, wherein the radially outward expansion force is sufficient to cause the tissue ingrowth to recede.

16. The system of claim 15, wherein the radially outward expansion force is 0.15 N or more.

17. The system of claim 13, wherein the first stent includes an inner surface having a first profile, and wherein the second stent includes an outer surface having a second profile, and wherein the first profile matches the second profile.

18. The system of claim 13, wherein the portion of the liner extending along the tissue ingrowth region is configured to deflect radially inward from the inner surface of the tubular scaffold.

19. The system of claim 18, wherein the liner extends continuously within the lumen of the first expandable scaffold.

* * * * *